US012582638B2

(12) United States Patent
Kim et al.

(10) Patent No.: US 12,582,638 B2
(45) Date of Patent: Mar. 24, 2026

(54) PHARMACEUTICAL COMPOSITION FOR TREATING CANCER, CONTAINING MTOR-SIGNALING INHIBITOR AS ACTIVE INGREDIENT

(71) Applicant: KOREA ADVANCED INSTITUTE OF SCIENCE AND TECHNOLOGY, Daejeon (KR)

(72) Inventors: Seyun Kim, Seoul (KR); Boah Lee, Seoul (KR); Seung Ju Park, Daejeon (KR)

(73) Assignee: KOREA ADVANCED INSTITUTE OF SCIENCE AND TECHNOLOGY, Daejeon (KR)

( * ) Notice: Subject to any disclaimer, the term of this patent is extended or adjusted under 35 U.S.C. 154(b) by 798 days.

(21) Appl. No.: 17/800,627

(22) PCT Filed: Feb. 19, 2021

(86) PCT No.: PCT/KR2021/002105

§ 371 (c)(1),
(2) Date: Aug. 18, 2022

(87) PCT Pub. No.: WO2021/167389

PCT Pub. Date: Aug. 26, 2021

(65) Prior Publication Data

US 2023/0346762 A1 Nov. 2, 2023

(30) Foreign Application Priority Data

Feb. 21, 2020 (KR) ........................ 10-2020-0021549

(51) Int. Cl.

| | |
|---|---|
| ***A61K 31/4468*** | (2006.01) |
| ***A61K 31/4745*** | (2006.01) |
| ***A61K 31/513*** | (2006.01) |
| ***A61K 39/00*** | (2006.01) |
| ***A61P 35/00*** | (2006.01) |
| ***C07K 16/28*** | (2006.01) |

(52) U.S. Cl.

CPC ...... *A61K 31/4468* (2013.01); *A61K 31/4745* (2013.01); *A61K 31/513* (2013.01); *A61K 39/00* (2013.01); *A61P 35/00* (2018.01); *C07K 16/2818* (2013.01); *A61K 2039/505* (2013.01)

(58) Field of Classification Search

CPC .................................................. A61K 31/4468

See application file for complete search history.

(56) References Cited

U.S. PATENT DOCUMENTS

| | | | |
|---|---|---|---|
| 2007/0254883 | A1 | 11/2007 | Crew et al. |
| 2014/0171456 | A1 | 6/2014 | Meng et al. |
| 2018/0125812 | A1 | 5/2018 | Chen et al. |

FOREIGN PATENT DOCUMENTS

| | | | |
|---|---|---|---|
| CN | 110234764 | A | 9/2019 |
| JP | 2014-012721 | A | 1/2014 |
| KR | 10-2013-0013264 | A | 2/2013 |
| KR | 10-2019-0139637 | A | 12/2019 |
| WO | WO-98/03174 | A1 | 1/1998 |
| WO | WO-2018/204416 | A1 | 11/2018 |
| WO | WO-2021/102279 | A1 | 5/2021 |

OTHER PUBLICATIONS

Zaniboni, Alberto. "New active drugs for the treatment of advanced colorectal cancer." World journal of gastrointestinal surgery vol. 7,12 (2015): 356-9. doi:10.4240/wjgs.v7.i12.356 (Year: 2015).*

Xie, Jianling et al. "mTOR inhibitors in cancer therapy." F1000Research vol. 5 F1000 Faculty Rev—2078. Aug. 25, 2016, doi: 10.12688/f1000research.9207.1 (Year: 2016).*

Lee, Boah et al. "Lomitapide, a cholesterol-lowering drug, is an anticancer agent that induces autophagic cell death via inhibiting mTOR." Cell death & disease vol. 13,7 603. Jul. 12, 2022, doi:10.1038/s41419-022-05039-6 (Year: 2022).*

TilakVijay, J., et al., "Virtual screening of novel compounds as potential ER& inhibitors", Bioinformation, 2019, vol. 15(5), pp. 321-332.

Office Action for corresponding JP Patent Application No. 2022-550038, dated Jan. 10, 2024.

"Bioassay Record Bioactivity DYAD Bioactivity for AID 1345084—SID 363680234", Sep. 28, 2018 (Sep. 28, 2018), XP093052637.

"Bioassay Record Bioactivity DYAD Bioactivity for AID 1345084—SID 363680234 (Supplementary information)", Sep. 28, 2018 (Sep. 28, 2018), XP093052640.

"Primary qHTS to identify gynecologic anti-cancer compounds using libraries of approved drugs and bioactive compounds", Sep. 28, 2018 (Sep. 28, 2018), p. 75, XP093052643.

First Office Action from Corresponding Chinese Application No. 202180015980.0, Dated May 25, 2023.

First Office Action from Corresponding Japanese Application No. 2022-550038, Dated Jul. 14, 2023.

Extended European Search Report from Corresponding European Application No. 21757494.6, Dated Jun. 16, 2023.

Biocell, 2018, 42(suppl.4), p. 54 LI-C09.

International Search Report from corresponding PCT Application No. PCT/KR2021/002105, dated Jun. 8, 2021.

Hua, H., et al.; "Targeting mTOR for cancer therapy", Journal of hematology and oncology, 2019, vol. 12, thesis No. 71, pp. 1-19.

(Continued)

*Primary Examiner* — Andrew D Kosar
*Assistant Examiner* — Connor K English
(74) *Attorney, Agent, or Firm* — Harness, Dickey & Pierce, P.L.C.

(57) ABSTRACT

The present invention relates to a pharmaceutical composition for preventing or treating cancer, containing a mTOR-signaling inhibitor as an active ingredient. The composition of the present invention exhibits the efficacy of inhibiting the growth of cancer cells and killing cancer cells, and thus can be used as an anticancer agent.

9 Claims, 43 Drawing Sheets

(56) References Cited

OTHER PUBLICATIONS

International Search Report from corresponding PCT Application No. PCT/KR2020/007922, dated Nov. 17, 2020.

* cited by examiner

* p vlaue<0.05,  p vlaue<0.01, * p vlaue<0.001

PHARMACEUTICAL COMPOSITION FOR TREATING CANCER, CONTAINING MTOR-SIGNALING INHIBITOR AS ACTIVE INGREDIENT

CROSS-REFERENCE TO RELATED APPLICATIONS

This application is a national phase application of PCT Application No. PCT/KR2021/002105, filed on Feb. 19, 2021, which claims benefit of Korean Patent Application No. 10-2020-0021549, filed on Feb. 21, 2020 and PCT Application No. PCT/KR2020/007922, filed on Jun. 18, 2020. The entire disclosure of the applications identified in this paragraph are incorporated herein by references.

TECHNICAL FIELD

The present disclosure relates to a pharmaceutical composition including an mTOR signaling inhibitor as an active ingredient for prevention or treatment of cancer.

BACKGROUND ART

Cancer is the most common and serious disease that threatens human health, and research and development of anticancer drugs are important for extending the life expectancy of cancer patients. In recent years, the rapid development of cancer genomics and molecular medicine and the development of new anticancer drugs have much advanced cancer therapies, but there is still a need for new therapeutic agents. Colorectal cancer is a malignant tumor in the appendix, colon, and rectum, which occurs at the mucous membrane, the innermost surface of the large intestine. In South Korea, colorectal cancer is the first common cancer after stomach cancer. Recent westernization of the dietary pattern has led to a steep increase in the incidence of colorectal cancer. In the last decade, the mortality of colorectal cancer has increased by about 80%, with the rate continuously increasing.

The treatment of colorectal cancer can be conducted by surgical dissection, chemotherapy, and radiotherapy. For polyps, which are in the pre-stage of colorectal cancer or for early-stage colorectal cancer localized on polyps, colonic polypectomy is curative. After the development of fluorouracil (5-FU) in the 1970s, chemotherapy has been used for both cancer of the colon and rectum, with the aid of the five antitumor agents irinotecan, oxaliplatin, capecitabine, TAS-102, and 5-FU, which were approved by the FDA. Also, application has been made of targeted therapy with the five approved agents cetuximab, panitumumab, bevacizumab, aflibercept, and regorafenib which target epidermal growth factor receptor (EGFR), vascular endothelial growth factor (VEGF), and vascular endothelial growth factor receptor (VEGF-R). However, it is still urgent to develop a colorectal cancer therapy that has excellent anticancer effects, stability, and in vivo absorptivity.

The mTOR (mechanistic target of rapamycin) protein, which functions as a serine/threonine kinase, is a core signaling pathway factor that regulates cellular processes including cell growth, cell cycle, protein synthesis, and glucose metabolism. Among others, mTOR is a critical protein responsible for cell growth signaling pathway and becomes abnormally active in 30% of solid cancer cells. In cancer cells, mTOR and its upstream factors (PI3K and Akt) are known to undergo the greatest modification. The activation of mTOR signals in cancer is caused by mutation of mTOR gene itself and the upstream oncogenes (PI3K and Akt) and tumor suppressors (e. g., PTEN and TSC1/2). Hence, suppression of the mTOR-associated signaling pathway may inhibit protein synthesis, lipid synthesis, and cell growth and provoke cell autophagy, culminating in cell death. Therefore, there is a need for developing an mTOR-associated signaling inhibitor to inhibit cancer cell growth and induce cancer cell death.

DISCLOSURE OF INVENTION

Technical Problem

Leading to the present disclosure, intensive and thorough research, conducted by the present inventors, into the development of a compound to inhibit cancer cell growth and induce cancer cell death, resulted in the finding that a composition including an mTOR signaling inhibitor as an active ingredient is effective for treating cancer.

Therefore, the present disclosure aims to provide a pharmaceutical composition including an mTOR signaling inhibitor as an active ingredient for prevention or treatment of cancer.

Solution to Problem

According to an aspect thereof, the present disclosure provides a pharmaceutical composition comprising an mTOR signaling inhibitor as an active ingredient for prevention or treatment of cancer.

The mTOR signaling inhibitor refers to a substance that inhibits the activity of mTOR itself or the activity of an upstream factor that upregulates the activity of mTOR. Examples of the targets the activity of which is down-regulated by the mTOR signaling inhibitor include mTOR, PI3K, Akt, S6K, and S6, but are not limited thereto.

In an embodiment of the present disclosure, the mTOR signaling inhibitor is lomitapide.

Lomitapide (sold under the brand names Jaxtapid (US) and Lojuxta (EU)) is an orphan drug used as a lipid-lowering agent for the treatment of familial hypercholesterolemia, developed by Aegerion Pharmaceuticals. The US Food and Drug Administration (FDA) approved lomitapide in Dec. 21, 2012, as an orphan drug to reduce LDL cholesterol, total cholesterol, apolipoprotein B, and non-high-density lipoprotein (non-HDL) cholesterol in people with homozygous familial hypercholesterolemia.

Lomitapide has the IUPAC name of N-(2,2,2-trifluoroethyl)-9-[4-[4-[[[4'-(trifluoromethyl)[1,1'-biphenyl]2-yl] carbonyl]amino]-1-piperidinyl]butyl]-9H-fluoren-9-carboxamide.

In an embodiment of the present disclosure, lomitapide is represented by the following Chemical Formula I:

[Chemical Formula I]

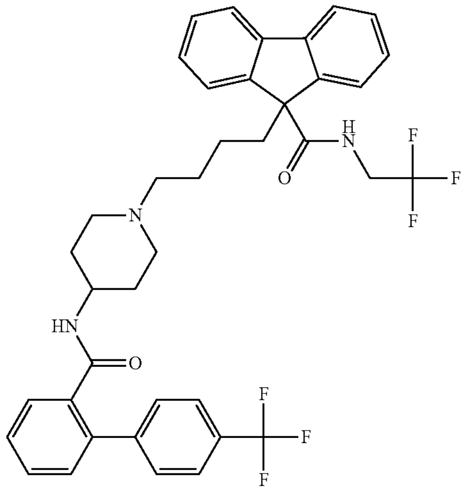

In an embodiment of the present disclosure, the mTOR signaling inhibitor may be lomitapide, a pharmaceutically acceptable salt thereof, or an optical isomer thereof.

In an embodiment of the present disclosure, the cancer is a solid cancer.

As used herein, the term "solid cancer" refers to a mass resulting from abnormal cellular growth in various solid organs such as the bladder, breast, bowel, kidney, lung, liver, brain, esophagus, gallbladder, ovary, pancreas, stomach, uterine cervix, thyroid gland, prostate, and skin, as opposed to blood cancer.

In an embodiment of the present disclosure, the solid cancer is selected from the group consisting of melanoma, brain tumor, benign astrocytoma, malignant astrocytoma, pituitary adenoma, meningioma, central nervous system lymphoma, oligodendroglioma, ependymoma, brain stem tumor, head and neck tumor, laryngeal cancer, oropharyngeal cancer, nasal cavity cancer, nasopharyngeal cancer, salivary gland cancer, hypopharyngeal cancer, thyroid cancer, oral cavity carcinoma, thoracic tumor, small cell lung cancer, non-small cell lung cancer, thymus cancer, mediastinal tumor, esophageal cancer, breast cancer, male breast cancer, celioma, stomach cancer, liver cancer, cholangiocarcinoma, bile duct cancer, pancreatic cancer, small bowel cancer, large bowel cancer, rectal cancer, anal cancer, bladder cancer, kidney cancer, male genital tumor, penis cancer, prostate cancer, female genital cancer, cervical cancer, endometrial cancer, ovarian cancer, uterine sarcoma, vaginal cancer, vulva cancer, female urethral cancer, bone tumor, duodenal cancer, fibrosarcoma, and skin cancer, but with no limitations thereto.

In an embodiment of the present disclosure, the cancer is a blood cancer.

As used herein, the term "blood cancer" refers to a type of cancer that affects constituents of blood and is intended to encompass malignant tumors generated in blood, hematopoietic organs, lymph nodes, lymphoid organs, etc.

In an embodiment of the present disclosure, the blood cancer is selected from the group consisting of acute myeloid leukemia, acute lymphocytic leukemia, chronic myeloid leukemia, chronic lymphocytic leukemia, acute monocytic leukemia, multiple myeloma, Hodgkin's lymphoma, and non-Hodgkin's lymphoma, but with no limitations thereto.

The composition of the present disclosure may contain a pharmaceutically acceptable carrier in addition to the active ingredient lomitapide, a pharmaceutically acceptable salt thereof, or an optical isomer thereof.

So long as it is typically used for formulations, any pharmaceutically acceptable carrier may be contained in the composition of the present disclosure. Examples of the pharmaceutically acceptable carrier include, but are not limited to, lactose, dextrose, sucrose, sorbitol, mannitol, starch, acacia gum, calcium phosphate, alginate, gelatin, calcium silicate, microcrystalline cellulose, polyvinylpyrrolidone, cellulose, water, syrup, methyl cellulose, methyl hydroxybenzoate, propyl hydroxybenzoate, talc, magnesium stearate, and mineral oil.

The pharmaceutical composition of the present disclosure may further contain, in addition to the above ingredients, a lubricant, a humectant, a sweetener, a flavorant, an emulsifier, a suspending agent, a preservative, and the like. For a detail of suitable pharmaceutically acceptable carriers and preparations, reference may be made of Remington's Pharmaceutical Sciences ($19^{th}$ ed., 1995).

The pharmaceutical composition of the present disclosure can be administered orally or parenterally via, for example, intrathecal, intravenous, subcutaneous, intradermal, intramuscular, intraperitoneal, intrasternal, intratumoral, intranasal, intracerebral, intracranial, intrapulmonary, and intrarectal routes, but with no limitations thereto.

A suitable dosage of the pharmaceutical composition of the present invention varies depending on factors such as formulation method, mode of administration, patient's age, weight, sex, pathological condition, and diet, the duration of administration, the route of administration, excretion rate, and response sensitivity, Usually, the skilled practitioner can easily determine and prescribe the effective dosage (pharmaceutically effective amount) for the desired treatment or prophylaxis. According to a preferred embodiment of the present disclosure, the daily dosage of the pharmaceutical composition of the present disclosure is in the range of 0.0001-100 mg/kg.

As used herein, the term "pharmaceutically effective amount" means an amount sufficient to prevent or treat the aforementioned diseases.

As used herein, the term "prevention" means prophylactic or protective treatment of a disease or disease state. As used herein, the term "treatment" refers to reduction, suppression, sedation or eradication of a disease state.

The pharmaceutical composition of the present disclosure is formulated using a pharmaceutically acceptable carrier and/or excipient, according to the method that is easily conducted by a person having ordinary skills in the art to which the present disclosure pertains, and the pharmaceutical composition may be prepared into a unit dosage form or may be inserted into a multidose container. Here, the dosage form may be prepared in various ways, such as oral formulation, injection formulation, etc., may be a solution in an oily or aqueous medium, a suspension, an emulsion, an extract, a powder, a suppository, a granule, a tablet, or a capsule, and may further contain a dispersant or a stabilizer.

According to an embodiment of the present disclosure, the pharmaceutical composition including lomitapide of the present disclosure has the effect of inhibiting the mTOR signaling pathway and upregulating the expression of a protein involved in an autophagy mechanism of cells.

The term "autophagy", as used herein, refers to the natural, conserved degradation of the cell that removes unnecessary or dysfunctional components through a cellular regulated mechanism.

There are autophagy-related genes including genes encoding for ULK1, mTOR, ATG family, and DDIT4.

ULK1, encoded by a ULK1 gene, is a protein kinase necessary for the initiation of autophagy. Under the condition of high mTOR activity, the activity of ULK1 is suppressed. When the mTOR activity is inhibited, ULK1 is activated to initiate the autophagy-related signaling.

mTOR, which is a protein kinase, is a core component which is essentially responsible for the inhibition of autophagy as well as the regulation of growth and activity of cells. mTOR mediates the regulation of autophagy by directly phosphorylating ULK1 and various autophagy proteins. In the condition of inhibiting mTOR activity, autophagy is actively promoted on the contrary.

Genes in the ATG family, which consist of about 30 autophagy-related genes, play pivotal roles in the onset and progression of autophagy. They are responsible for the overall process of autophagy including the initiation of autophagy, the formation of autophagy membranes, the recognition of a substrate to be degraded, and the fusion of autophagy membranes with liposomes.

DDIT4, also known as REDD1, regulates mTOR via TSC protein. Thus, an increased level of DDIT4 induces the downregulation of mTOR, leading to an increase in autophagy activity.

According to an embodiment of the present disclosure, the pharmaceutical composition of the present disclosure has the effect of suppressing the growth of cancer cells and inhibiting the growth of tumor in vivo. Therefore, the pharmaceutical composition of the present disclosure has inhibitory activity against cancer, especially, melanoma, blood cancer, skin cancer, colorectal cancer, brain cancer, ovarian cancer, bladder cancer, breast cancer, uterine cancer, duodenal cancer, fibrosarcoma, kidney cancer, liver cancer, lung cancer, pancreatic cancer, stomach cancer, prostate cancer, bone tumor, and endometrial cancer.

In an embodiment of the present disclosure, the composition may further include an anticancer agent.

In an embodiment of the present disclosure, the anticancer agent may be selected from the group consisting of fluorouracil, irinotecan, an anti-PD1 antibody, bevacizumab, capecitabine, cetuximab, ramucirumab, oxaliplatin, ipilimumab, pembrolizumab, leucovorin, trifluridine/tipiracil, nivolumab, panitumumab, regorafenib, aflibercept, and a combination thereof.

In an embodiment of the present disclosure, the anticancer agent may be selected from the group consisting of fluorouracil, irinotecan, an anti-PD1 antibody, and a combination thereof.

In an embodiment of the present disclosure, the composition may contain lomitapide at a concentration of 0.5 to 6 μM.

According to an embodiment of the present disclosure, a combination of 0.5 to 6 μM of lomitapide and 1 to 12 μM of fluorouracil exhibits a synergistic anticancer effect against the colorectal cancer cell line HCT116, more specifically, with the highest synergistic peak detected in a combination of 0.5 to 1.25 μM of lomitapide and 1.25 to 5 μM of fluorouracil.

According to an embodiment of the present disclosure, a combination of 1.25 to 6 μM of lomitapide and 1 to 12 μM of irinotecan exhibits a synergistic anticancer effect against the colorectal cancer cell line HCT116, more specifically, with the highest synergistic peak detected in a combination of 2.5 to 6 μM of lomitapide and 1.25 to 5 μM of irinotecan.

According to an embodiment of the present disclosure, a combination of 0.5 to 1.25 μM of lomitapide and 10 to 22 μM of fluorouracil exhibits a synergistic anticancer effect against the colorectal cancer cell line HT29, According to an embodiment of the present disclosure, a combination of 0.5 to 2.75 μM of lomitapide and 4 to 22 μM of irinotecan exhibits a synergistic anticancer effect against the colorectal cancer cell line HT29, more specifically, with the highest synergistic peak detected in a combination of 0.625 to 2.5 μM of lomitapide and 5 to 20 μM of irinotecan.

According to an embodiment of the present disclosure, a combination of 2 to 3 μM of lomitapide and 12.5 to 110 μM of fluorouracil exhibits a synergistic anticancer effect against the colorectal cancer cell line SW480.

According to an embodiment of the present disclosure, a combination of 2 to 3 μM of lomitapide and 0.6 to 60 μM of irinotecan exhibits a synergistic anticancer effect against the colorectal cancer cell line SW480, more specifically, with the highest synergistic peak detected in a combination of 2 to 3 μM of lomitapide and 0.6 to 1.56 or 6.25 to 60 μM of irinotecan.

PD-1 is a key immune checkpoint receptor expressed by activated T and B cells and mediates immunosuppression. PD-1 is a member of the CD28 family of receptors, which include CD28, CTLA-4, ICOS, PD-1, and BTLA. Two cell surface glycoprotein ligands for PD-1 have been identified: programmed death-1 (PD-L1) and programmed death ligand-2 (PD-L2). These ligands are expressed on various human cancer cells as well as antigen-presenting cells and have been shown to downregulate cytokine secretion and T cell activation upon binding to PD-1. Inhibition of the PD-1/PD-L1 interaction mediates potent antitumor activity in preclinical models.

According to another aspect thereof, the present disclosure provides a method for prevention or treatment of cancer, the method comprising a step of administering to a subject a pharmaceutical composition comprising the mTOR signaling inhibitor of the present disclosure as an active ingredient.

As used herein, the term "administration" or "administer" refers to the direct application of a therapeutically effective amount of the composition of the present disclosure to a subject (i.e., an object) which suffers from or is likely to suffer from the diseases, thereby forming the same amount thereof in the body of the subject.

The term "therapeutically effective amount" of the composition refers to the content of the composition, which is sufficient to provide a therapeutic or prophylactic effect to a subject to be administered, and thus the term has a meaning including "prophylactically effective amount".

As used herein, the term "subject" is intended to encompass mammals including humans, mice, rats, guinea pigs, dogs, cats, horses, cow, pigs, monkeys, chimpanzee, baboon, or rhesus monkeys. Specifically, the subject of the present disclosure is a human.

In an embodiment of the present disclosure, the step of administering the pharmaceutical composition to a subject may be conducted in combination with an anticancer agent.

In an embodiment of the present disclosure, the anticancer agent is selected from the group consisting of fluorouracil, irinotecan, an anti-PD1 antibody, and a combination thereof.

Since the method for preventing or treating cancer of the present disclosure includes a step of administering the pharmaceutical composition according to an aspect of the present disclosure, the overlapping descriptions therebetween are omitted to avoid undue complexity of the specification.

Advantageous Effects of Invention

Features and advantages of the present disclosure are summarized as follows:

The present disclosure provides a pharmaceutical composition comprising an mTOR signaling inhibitor as an active ingredient for prevention or treatment of cancer.

The composition of the present disclosure exhibits the efficacy of suppressing the growth of cancer cells and killing cancer cells and as such, can be used as an anticancer agent.

MODE FOR CARRYING OUT THE INVENTION

A better understanding of the present disclosure may be obtained through the following examples, which are set forth to illustrate, but are not to be construed to limit the present disclosure.

EXAMPLES

Throughout the description, the term "%" used to express the concentration of a specific material, unless otherwise particularly stated, refers to (wt/wt) % for solid/solid, (wt/vol) % for solid/liquid, and (vol/vol) % for liquid/liquid.

Example 1: Cell Culture Method

NCM460 (human colon normal cell), HCT116 (human colon cancer cell, p53 wild-type), HT29 (human colon cancer cell, p53 mutant), SW480 (human colon cancer cell, p53 mutant), MDA-MB-231 (human breast cancer cell), MDA-MB-468 (human breast cancer cell), HS746T (human stomach cancer cell), SNU1 (human stomach cancer cell), SNU2 (human stomach cancer cell), MC38 (mouse colorectal cancer cell), and B16F10 (mouse melanoma cell) were purchased from ATCC (American Type Culture Collection, Virginia, USA).

NCM460 and HCT116 cells were cultured in McCoy's 5a medium (Sigma Aldrich, Missouri, USA) supplemented with 2 mM glutamine, 1% penicillin-streptomycin, and 10% fetal bovine serum (FBS) at 37° C. under 5% $CO_2$. HT29 and SW480 cells were cultured RPMI medium (Sigma Aldrich, Missouri, USA) supplemented with 2 mM glutamine, 1% penicillin-streptomycin, and 10% fetal bovine serum (FBS) at 37° C. under 5% $CO_2$. MDA-MB-231, MDA-MB-468, HS746T, and MC38, B16F10 cells were cultured in DMEM medium (Sigma Aldrich, Missouri, USA) supplemented with 2 mM glutamine, 1% penicillin-streptomycin, and 10% fetal bovine serum (FBS) at 37° C. under 5% $CO_2$. SNU1 and SNU2 cells were cultured in RPMI medium (Sigma Aldrich, Missouri, USA) supplemented with 2 mM glutamine, 1% penicillin-streptomycin, 25 mM HEPES, 25 mM $NaHCO_3$, and 10% fetal bovine serum (FBS) at 37° C. under 5% $CO_2$.

Example 2: Viability Assay for Lomitapide-Treated Cells

Example 2-1. Viability Assay for Lomitapide-Treated Colorectal Cells

NCM460, HCT116, HT29, and SW480 cell lines were each seeded at a density of $10^4$ cells/well into 96-well plates and incubated 37° C. for 24 hours before treatment with various concentrations (0, 1, 2, 5, and 10 μM) of lomitapide (Sigma Aldrich, Missouri, USA). After treatment of the cells with lomitapide at 37° C. for 24 in a 5% $CO_2$ atmosphere, 100 μL of an assay reagent (CellTiter-Glo® Reagent) was added to each well. Then, luminescence was read using VICTOR X Multilabel Reader (PerkinElmer, Massachusetts, USA) and used to calculate cell viability (%). Results are depicted in FIGS. 2 to 4.

Figure 1:
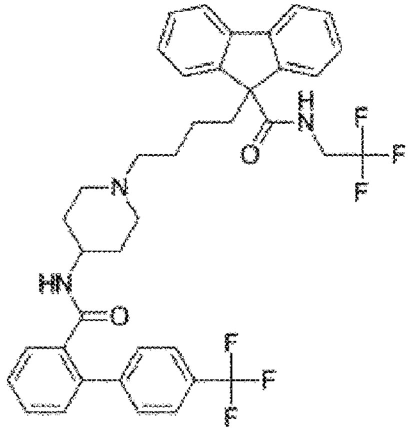
FIG. 1 shows the chemical formula of lomitapide.
Figure 2:
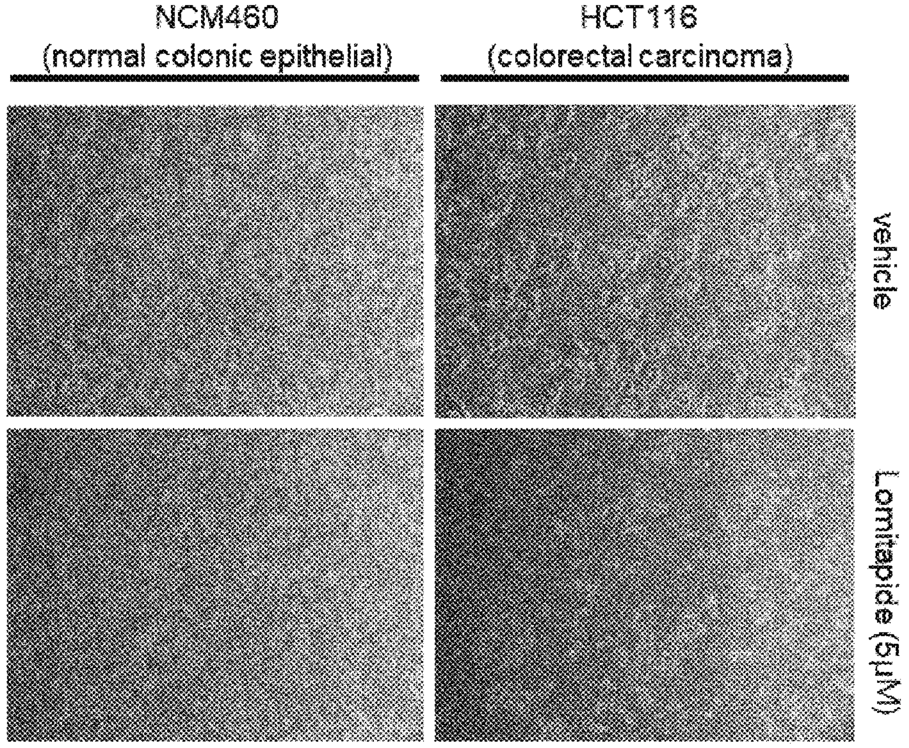
FIG. 2 shows morphological images of normal human colonic epithelial cells and colorectal cancer cell line HCT116 after treatment with the control drug DMSO and lomitapide.

Through this assay, a decreased cell viability was detected in the cancer cells treated with lomitapide, compared to normal cells (FIG. 2). The results indicate that lomitapide has an anticancer effect specific for cancer cells.

Figure 3:
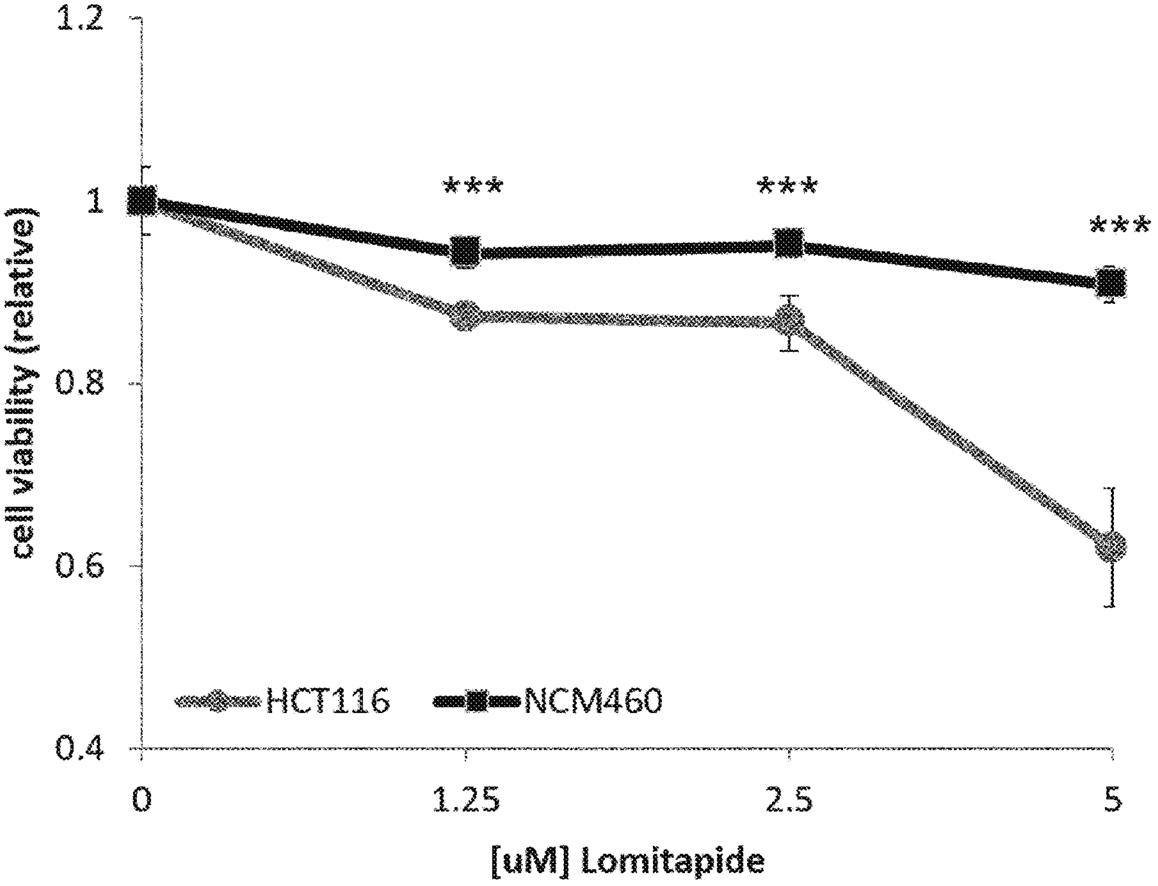
FIG. 3 is a plot of cell viability of normal human colonic epithelial cells and colorectal cancer cell line HCT116 after treatment with the control drug DMSO and lomitapide.
Figure 4:
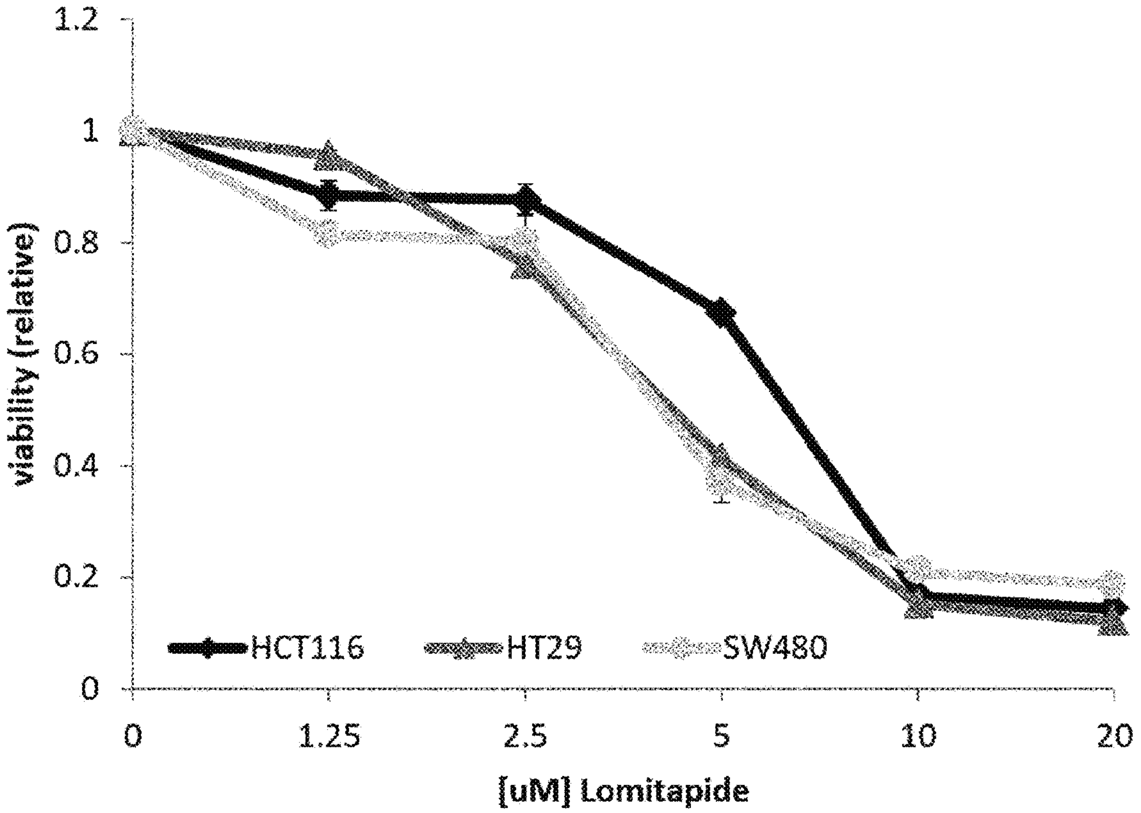
FIG. 4 is a plot of cell viability of the three representative colorectal cancer cell lines (HCT116, HT29, and SW480) after treatment with the control drug DMSO and lomitapide.
Figure 5A:
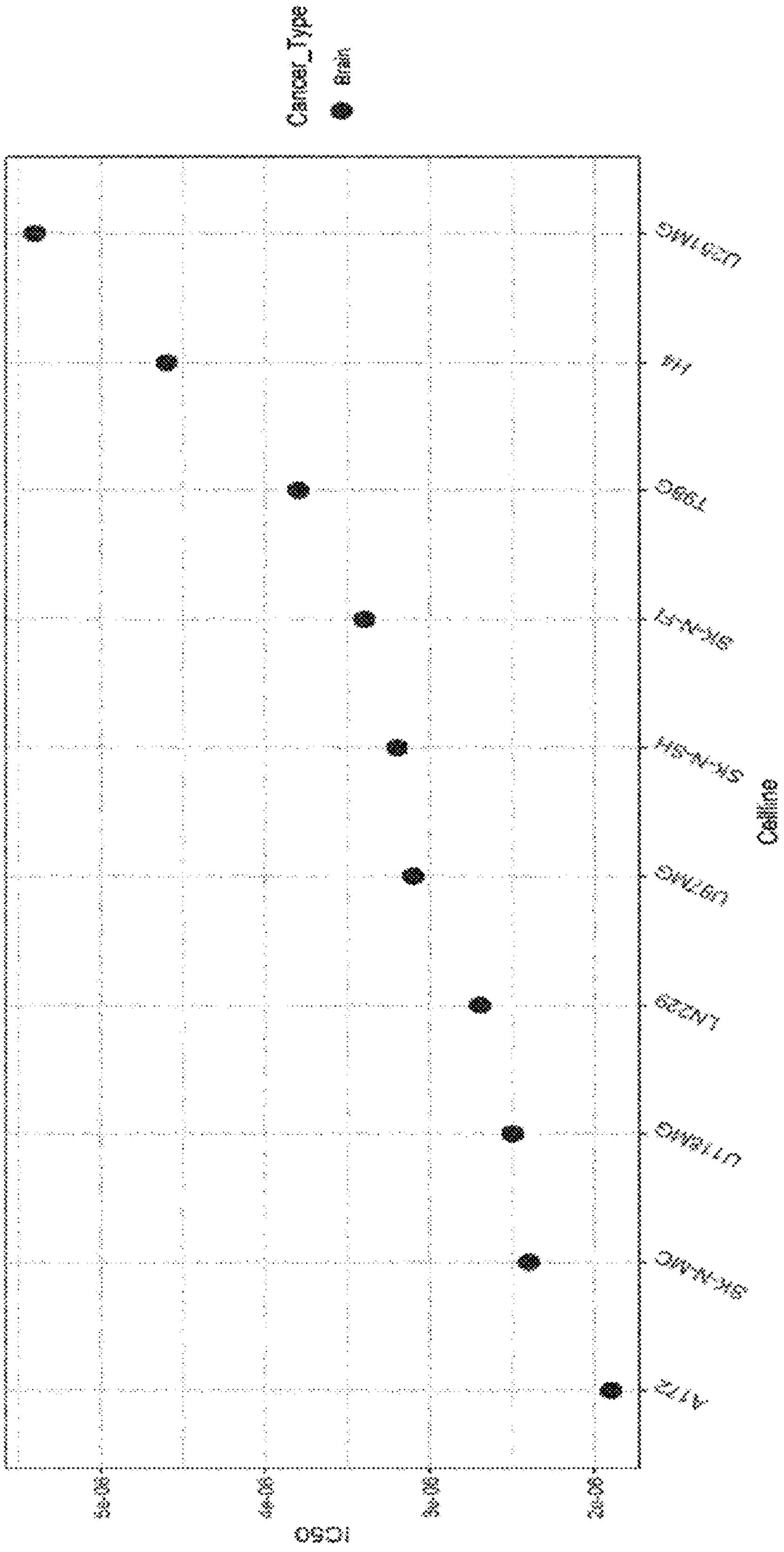
FIG. 5*a* shows assay results of cell viability for brain cancer cell lines after treatment with lomitapide.
Figure 5B:
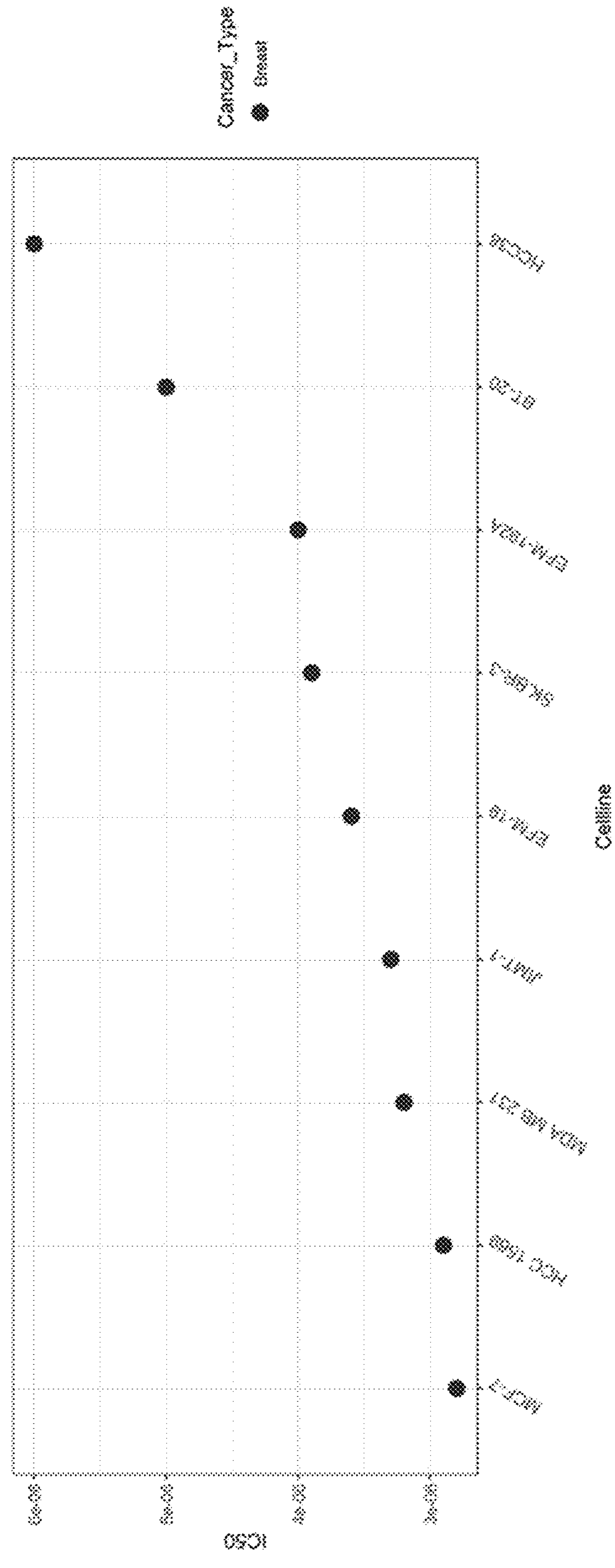
FIG. 5*b* shows assay results of cell viability for breast cancer cell lines after treatment with lomitapide.
Figure 5C:
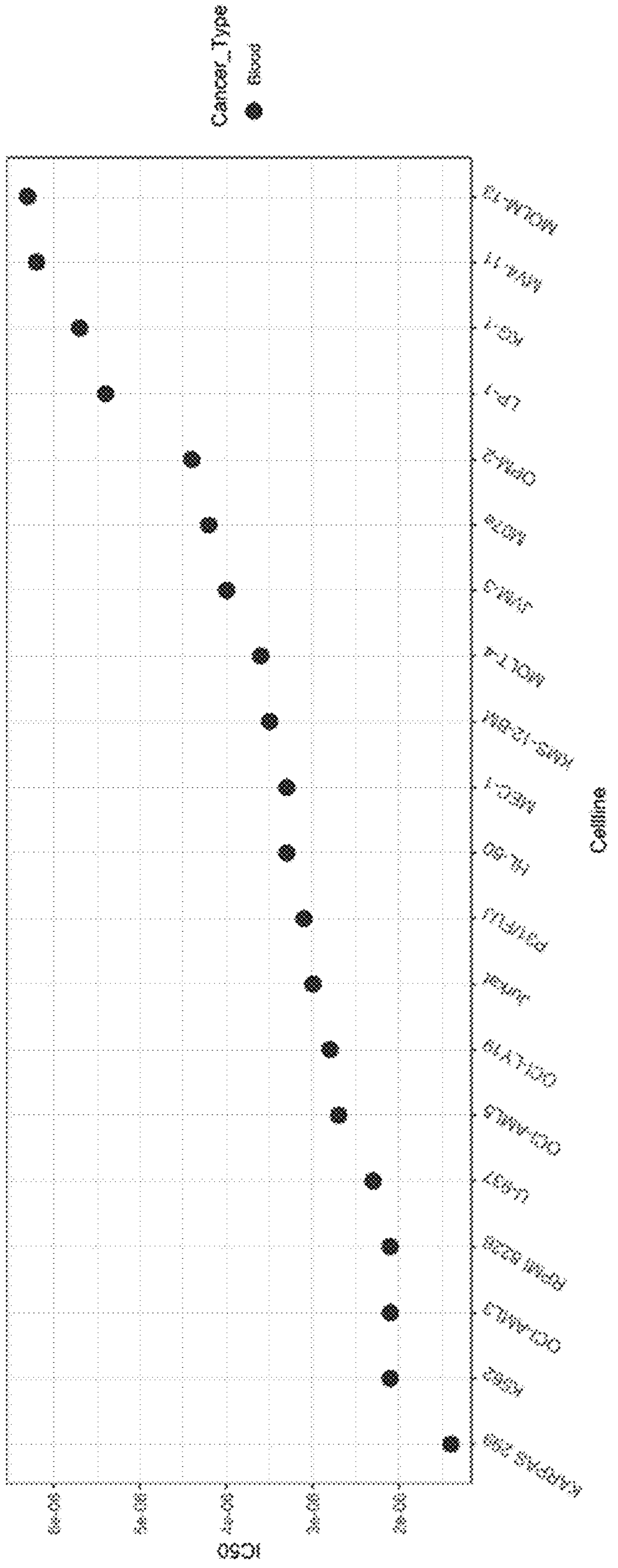
FIG. 5*c* shows assay results of cell viability for blood cancer cell lines after treatment with lomitapide.
Figure 5D:
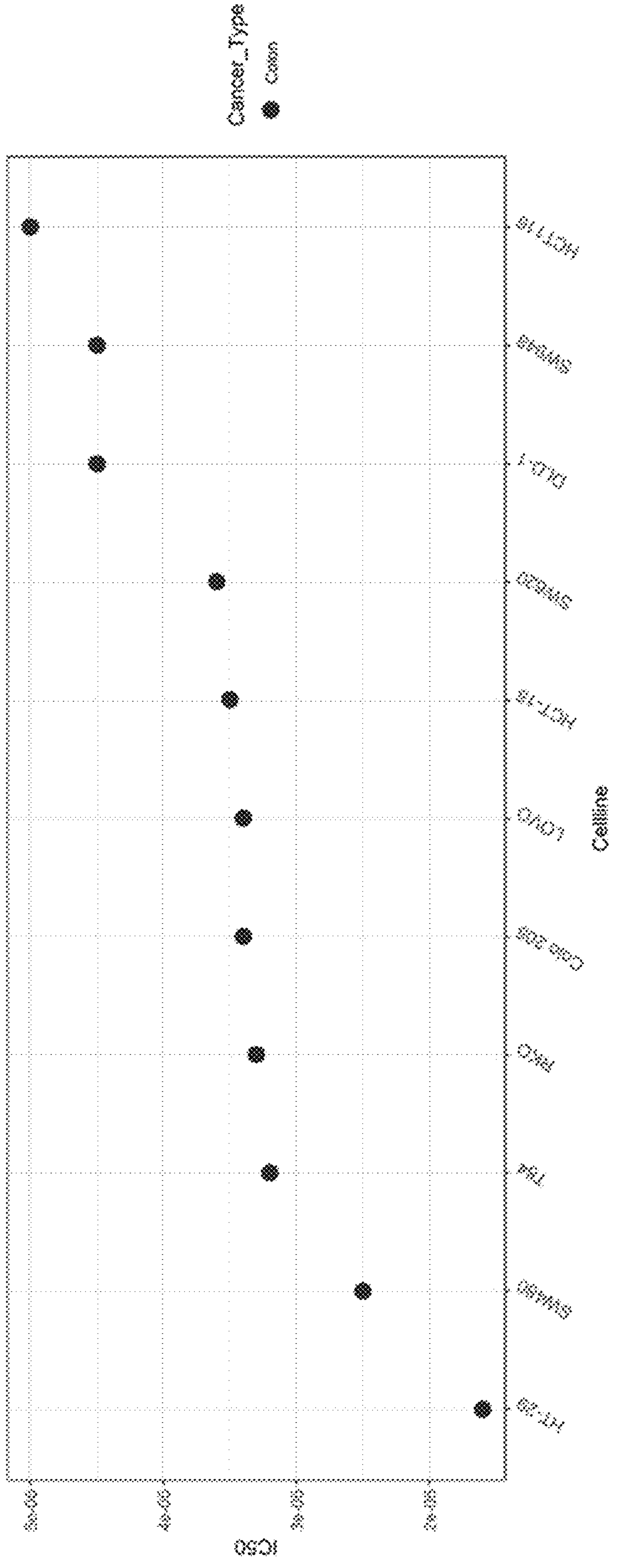
FIG. 5*d* shows assay results of cell viability for colon cancer cell lines after treatment with lomitapide.
Figure 5E:
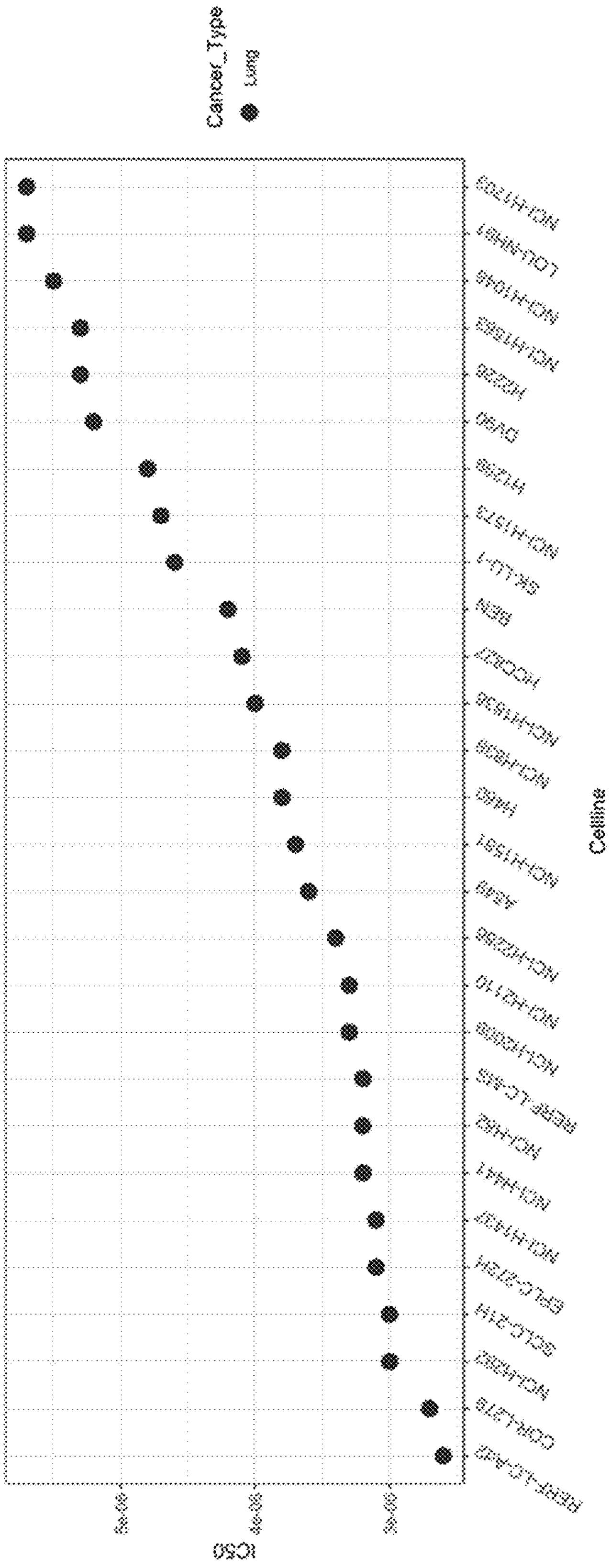
FIG. 5*e* shows assay results of cell viability for lung cancer cell lines after treatment with lomitapide.
Figure 5F:
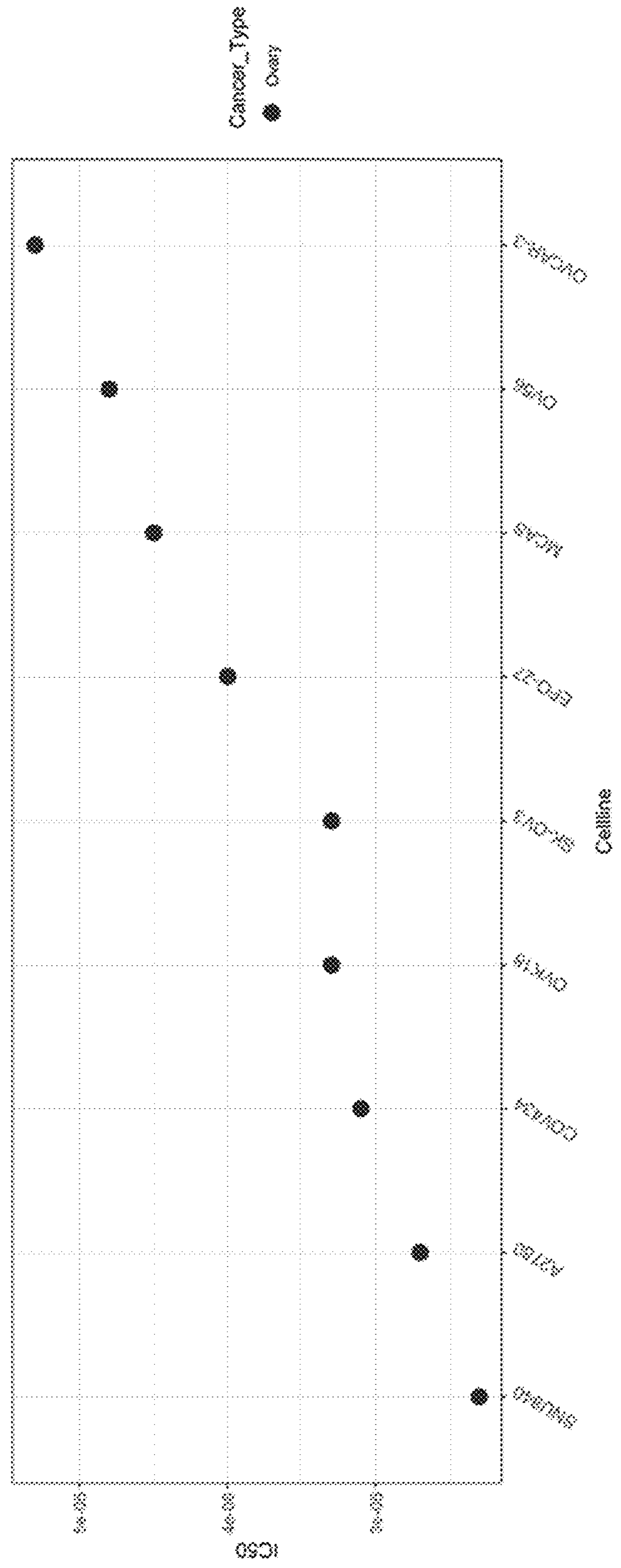
FIG. 5*f* shows assay results of cell viability for ovarian cancer cell lines after treatment with lomitapide.
Figure 5G:
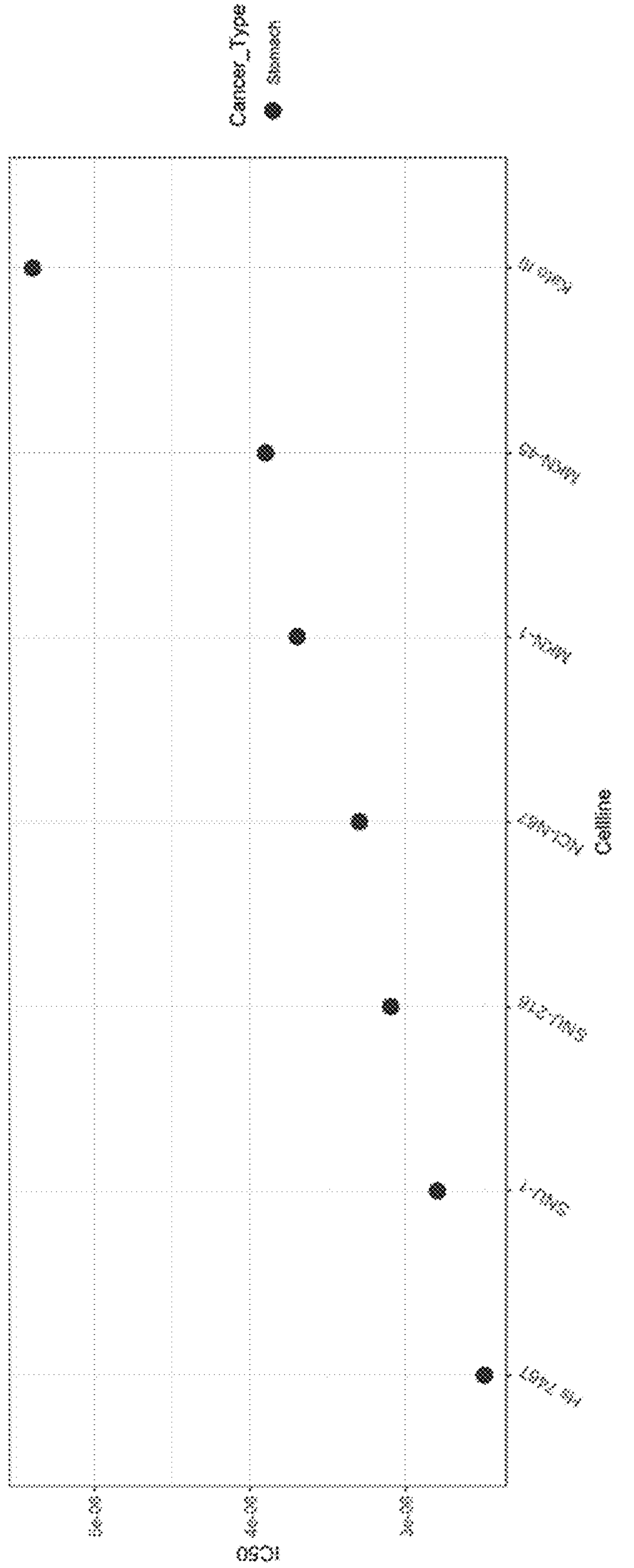
FIG. 5*g* shows assay results of cell viability for stomach cancer cell lines after treatment with lomitapide.
Figure 5H:
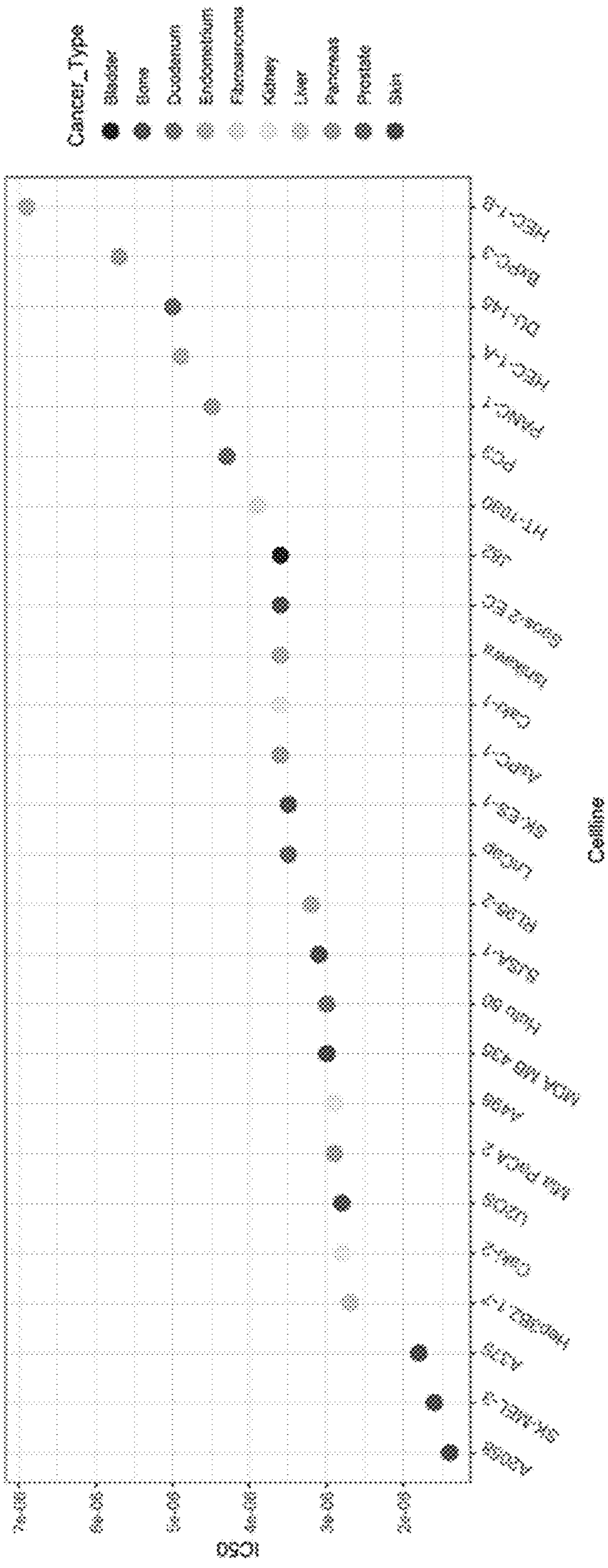
FIG. 5*h* shows assay results of cell viability for bladder cancer, bone cancer, duodenal cancer, endometrial cancer, fibrosarcoma, kidney cancer, liver cancer, pancreatic cancer, prostate cancer, skin cancer, and melanoma cell lines after treatment with lomitapide.

In addition, as identified in the assay, lomitapide reduced the viability of the three representative colorectal cancer cell lines (HCT116, HT29, and SW480) in a dose-dependent manner (FIGS. 3 and 4).

The results show that lomitapide is very effective for killing various colorectal cancer cells.

Example 2-2. Viability Assay for Lomitapide-Treated Cancer Cells

In addition to the colorectal cells, 120 cancer cell lines treated with various concentrations of lomitapide were assayed for viability.

To analyze cell viability, the cells were incubated with lomitapide at 37° C. for 72 hours in a 5% or 10% $CO_2$ atmosphere and then equilibrated at room temperature for 1 hour, followed by addition of CellTiterGlo reagent (Promega). One hour later, luminescence was measured to calculate cell viability (%). The 120 cell lines were purchased from ATCC (American Type Culture Collection, Virginia, USA).

Assay results of the various cancer cell lines are summarized as follows (Table 1 and FIGS. 5*a* to 5*h*).

TABLE 1

| No. | Cell Name | IC50 (μM) | Target Organ |
|---|---|---|---|
| 1 | A172 | 1.90 | Brain |
| 2 | A2058 | 1.40 | Skin |
| 3 | A2780 | 2.70 | Ovary |
| 4 | A375 | 1.80 | Skin |
| 5 | A498 | 2.90 | Kidney |
| 6 | A549 | 3.60 | Lung |
| 7 | AsPC-1 | 3.60 | Pancreas |
| 8 | BEN | 4.20 | Lung |
| 9 | BT-20 | 5.00 | Breast |
| 10 | BxPC-3 | 5.70 | Pancreas |
| 11 | Caki-1 | 3.60 | Kidney |
| 12 | Caki-2 | 2.80 | Kidney |
| 13 | Colo 205 | 3.40 | Colon |
| 14 | COR-L279 | 2.70 | Lung |
| 15 | COV434 | 3.10 | Ovary |
| 16 | DLD-1 | 4.50 | Colon |
| 17 | DU-145 | 5.00 | Prostate |
| 18 | DV90 | 5.20 | Lung |

TABLE 1-continued

| No. | Cell Name | IC50 (μM) | Target Organ |
|---|---|---|---|
| 19 | EFM-19 | 3.60 | Breast |
| 20 | EFM-192A | 4.00 | Breast |
| 21 | EFO-27 | 4.00 | Ovary |
| 22 | EPLC-272H | 3.10 | Lung |
| 23 | H1299 | 4.80 | Lung |
| 24 | H2228 | 5.30 | Lung |
| 25 | H4 | 4.60 | Brain |
| 26 | H460 | 3.80 | Lung |
| 27 | HCC 1569 | 2.90 | Breast |
| 28 | HCC38 | 6.00 | Breast |
| 29 | HCC827 | 4.10 | Lung |
| 30 | HCT116 | 5.00 | Colon |
| 31 | HCT-15 | 3.50 | Colon |
| 32 | HEC-1-A | 4.90 | Endometrium |
| 33 | HEC-1-B | 6.90 | Endometrium |
| 34 | Hep3B2.1-7 | 2.70 | Liver |
| 35 | HL-60 | 3.30 | Blood |
| 36 | Hs 746T | 2.50 | Stomach |
| 37 | HT-1080 | 3.90 | Fibrosarcoma |
| 38 | HT-29 | 1.60 | Colon |
| 39 | Hutu 80 | 3.00 | Duodenum |
| 40 | Ishikawa | 3.60 | Endometrium |
| 41 | J82 | 3.60 | Bladder |
| 42 | JIMT-1 | 3.30 | Breast |
| 43 | Jurkat | 3.00 | Blood |
| 44 | JVM-3 | 4.00 | Blood |
| 45 | K562 | 2.10 | Blood |
| 46 | KARPAS 299 | 1.40 | Blood |
| 47 | Kato III | 5.40 | Stomach |
| 48 | KG-1 | 5.70 | Blood |
| 49 | KMS-12-BM | 3.50 | Blood |
| 50 | LN229 | 2.70 | Brain |
| 51 | LnCap | 3.50 | Prostate |
| 52 | LOU-NH91 | 5.70 | Lung |
| 53 | LOVO | 3.40 | Colon |
| 54 | LP-1 | 5.40 | Blood |
| 55 | M07e | 4.20 | Blood |
| 56 | MCAS | 4.50 | Ovary |
| 57 | MCF-7 | 2.80 | Breast |
| 58 | MDA MB 231 | 3.20 | Breast |
| 59 | MDA MB 435 | 3.00 | Skin |
| 60 | MEC-1 | 3.30 | Blood |
| 61 | Mia PaCA 2 | 2.90 | Pancreas |
| 62 | MKN-1 | 3.70 | Stomach |
| 63 | MKN-45 | 3.90 | Stomach |
| 64 | MOLM-13 | 6.30 | Blood |
| 65 | MOLT-4 | 3.60 | Blood |
| 66 | MV4-11 | 6.20 | Blood |
| 67 | NCI-H1048 | 5.50 | Lung |
| 68 | NCI-H1437 | 3.10 | Lung |
| 69 | NCI-H1563 | 5.30 | Lung |
| 70 | NCI-H1573 | 4.70 | Lung |
| 71 | NCI-H1581 | 3.70 | Lung |
| 72 | NCI-H1703 | 5.70 | Lung |
| 73 | NCI-H1838 | 4.00 | Lung |
| 74 | NCI-H2009 | 3.30 | Lung |
| 75 | NCI-H2110 | 3.30 | Lung |
| 76 | NCI-H2286 | 3.40 | Lung |
| 77 | NCI-H292 | 3.00 | Lung |
| 78 | NCI-H441 | 3.20 | Lung |
| 79 | NCI-H82 | 3.20 | Lung |
| 80 | NCI-H838 | 3.80 | Lung |
| 81 | NCI-N87 | 3.30 | Stomach |
| 82 | OCI-AML3 | 2.10 | Blood |
| 83 | OCI-AML5 | 2.70 | Blood |
| 84 | OCI-LY19 | 2.80 | Blood |
| 85 | OPM-2 | 4.40 | Blood |
| 86 | OV56 | 4.80 | Ovary |
| 87 | OVCAR-3 | 5.30 | Ovary |
| 88 | OVK18 | 3.30 | Ovary |
| 89 | P31/FUJ | 3.10 | Blood |
| 90 | PANC-1 | 4.50 | Pancreas |
| 91 | PC3 | 4.30 | Prostate |
| 92 | RERF-LC-Ad2 | 2.60 | Lung |
| 93 | RERF-LC-MS | 3.20 | Lung |
| 94 | RKO | 3.30 | Colon |
| 95 | RL95-2 | 3.20 | Endometrium |
| 96 | RPMI 8226 | 2.10 | Blood |
| 97 | Saos-2 EC | 3.60 | Bone |
| 98 | SCLC-21H | 3.00 | Lung |
| 99 | SJSA-1 | 3.10 | Bone |
| 100 | SK.BR-3 | 3.90 | Breast |
| 101 | SK-ES-1 | 3.50 | Bone |
| 102 | SK-LU-1 | 4.60 | Lung |
| 103 | SK-MEL-3 | 1.60 | Skin |
| 104 | SK-N-FI | 3.40 | Brain |
| 105 | SK-N-MC | 2.40 | Brain |
| 106 | SK-N-SH | 3.20 | Brain |
| 107 | SK-OV3 | 3.30 | Ovary |
| 108 | SNU-1 | 2.80 | Stomach |
| 109 | SNU-216 | 3.10 | Stomach |
| 110 | SNU840 | 2.30 | Ovary |
| 111 | SW480 | 2.50 | Colon |
| 112 | SW620 | 3.60 | Colon |
| 113 | SW948 | 4.50 | Colon |
| 114 | T84 | 3.20 | Colon |
| 115 | T98G | 3.80 | Brain |
| 116 | U118MG | 2.50 | Brain |
| 117 | U251MG | 5.40 | Brain |
| 118 | U2OS | 2.80 | Bone |
| 119 | U87MG | 3.10 | Brain |
| 120 | U-937 | 2.30 | Blood |

Through the assay, it was found that even a very low concentration of lomitapide has an anticancer effect on various carcinomas and cancer cell lines including melanoma, blood cancer, skin cancer, colorectal cancer, brain cancer, ovarian cancer, bladder cancer, breast cancer, uterine cancer, duodenal cancer, fibrosarcoma, kidney cancer, liver cancer, lung cancer, pancreatic cancer, prostate cancer, stomach cancer, bone tumor, and endometrial cancer.

Example 3: Cell Signaling Assay for Lomitapide-Treated Cells

Example 3-1. Cell Signaling Assay for Lomitapide-Treated Colorectal and Breast Cancer Cells To confirm the function of lomitapide in HCT116, SW480, HT29, MDA-MB-231, and MDA-MB-468 cell lines, examination was made of cell signaling effects in the cells upon addition of lomitapide.

Cells treated with various concentrations (0, 5, and 10 μM) of lomitapide were lysed with RIPA buffer containing a protease-inhibitor cocktail. The whole-cell lysate was incubated on ice for 30 minutes. After centrifugation at 4° C. and 13,300×g for 15 minutes, the supernatant was collected. For use as controls, HCT116, SW480, HT29, MDA-MB-231, and MDA-MB-468 cells were treated with 1 μM of torin, known as an mTOR inhibitor.

For western blot analysis, the supernatant was loaded onto 10% SDS-PAGE gel. The separated proteins were blotted onto a PVDF membrane. Then, the blots were incubated with antibodies at 4° C. for 12 hours as follows (Table 2).

TABLE 2

| Cell | Antibody |
|---|---|
| HCT116 | anti-p-AKT, anti-p-mTOR, anti-p-S6K, anti-p-S6, anti-p-ERK, anti-AKT, anti-S6K, anti-S6 (Cell Signaling Technology, Massachusetts, USA), anti-alpha-tublin antibody(Sigma Aldrich, Missouri, USA) |

TABLE 2-continued

| Cell | Antibody |
| --- | --- |
| SW480<br>HT29<br>MDA-MB-231<br>MDA-MB-468 | anti-p-S6K, anti-p-S6, anti-S6K, anti-S6, anti-LC3(Cell Signaling Technology), anti-alpha-tublin antibody (Sigma Aldrich) |

Then, the blots were washed with TBST (a mixture of tris-buffered saline (TBS) and Tween 20), incubated with horseradish peroxidase-conjugated secondary antibody (Cell signaling) at 37° C. for 1 hour, and washed, followed by detecting enhanced chemiluminescence (ECL; Amersham).

Figure 6:
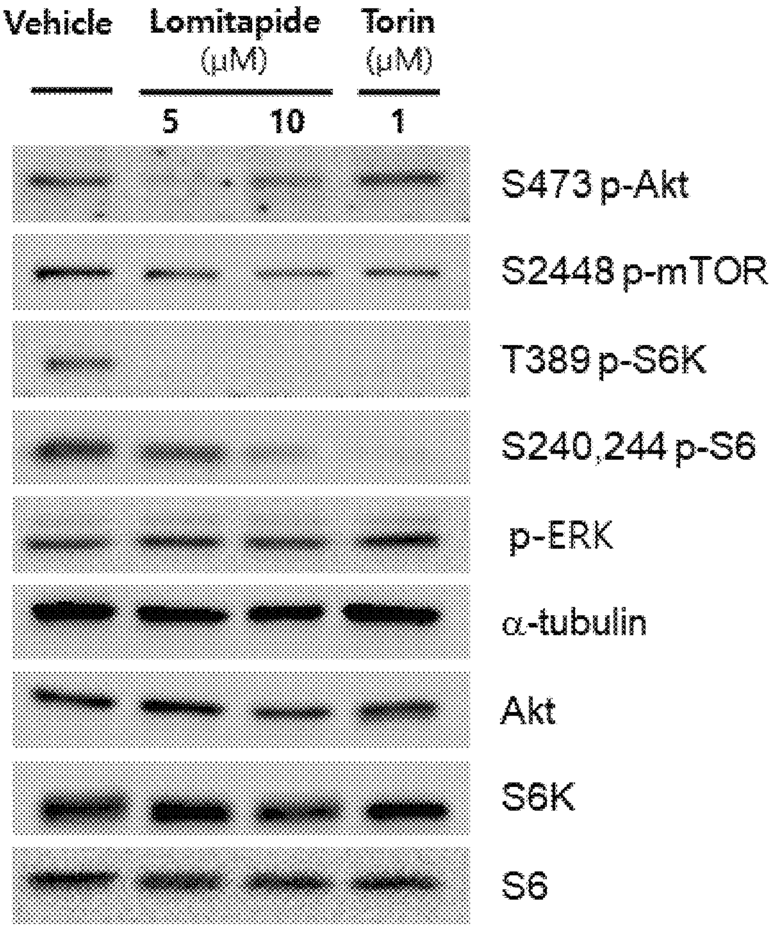
FIG. 6 shows western blotting analysis results of mTOR signaling-related proteins for the colorectal cancer cell line HCT116 after treatment with the control drug DMSO and lomitapide.

Through the experiments, it was identified that lomitapide decreased phosphorylation of target proteins levels (p-AKT, p-mTOR, p-S6K, p-S6) in a dose-dependent manner in HCT116 (FIG. 6). In addition, lomitapide remarkably decreased phosphorylation levels of target proteins (p-S6K and p-S6) and increased induction of conversion from LC3I into LC3II in SW480, HT29, MDA-MB-231, and MDA-MB-468 (FIGS. 7*a* to 7*d*). This result implies that lomitapide is highly effective for inhibiting mTOR and its upstream signaling pathway (AKT, p-S6K, and p-S6).

Example 3-2. Cell Signaling Assay for Lomitapide-Treated Stomach Cancer Cells

To confirm the function of lomitapide in HS746T, SNU1, and SNU2 cell lines, examination was made of cell signaling effects in the cells upon addition of lomitapide.

Cells treated with various concentration (0, 5, and 10 μM) of lomitapide were lysed with RIPA buffer containing a protease-inhibitor cocktail. The whole-cell lysate was incubated on ice for 30 minutes. After centrifugation at 4° C. and 13,300×g for 15 minutes, the supernatant was collected. For use as controls, cells were treated with 1 μM of torin, known as an mTOR inhibitor.

For western blot analysis, the supernatant was loaded onto 10% SDS-PAGE gel. The separated proteins were blotted onto a PVDF membrane. Then, the blots were incubated with antibodies at 4° C. for 12 hours as follows (Table 3).

TABLE 3

| Cell | Antibody |
| --- | --- |
| HS746T<br>SNU1 | anti-p-S6K, anti-p-S6, anti-S6K, anti-S6, anti-LC3(Cell Signaling Technology), anti-alpha-tublin antibody (Sigma Aldrich) |

Then, the blots were washed with TBST (a mixture of tris-buffered saline (TBS) and Tween 20), incubated with horseradish peroxidase-conjugated secondary antibody (Cell signaling) at 37° C. for 1 hour, and washed, followed by detecting enhanced chemiluminescence (ECL; Amersham).

Figure 7A:
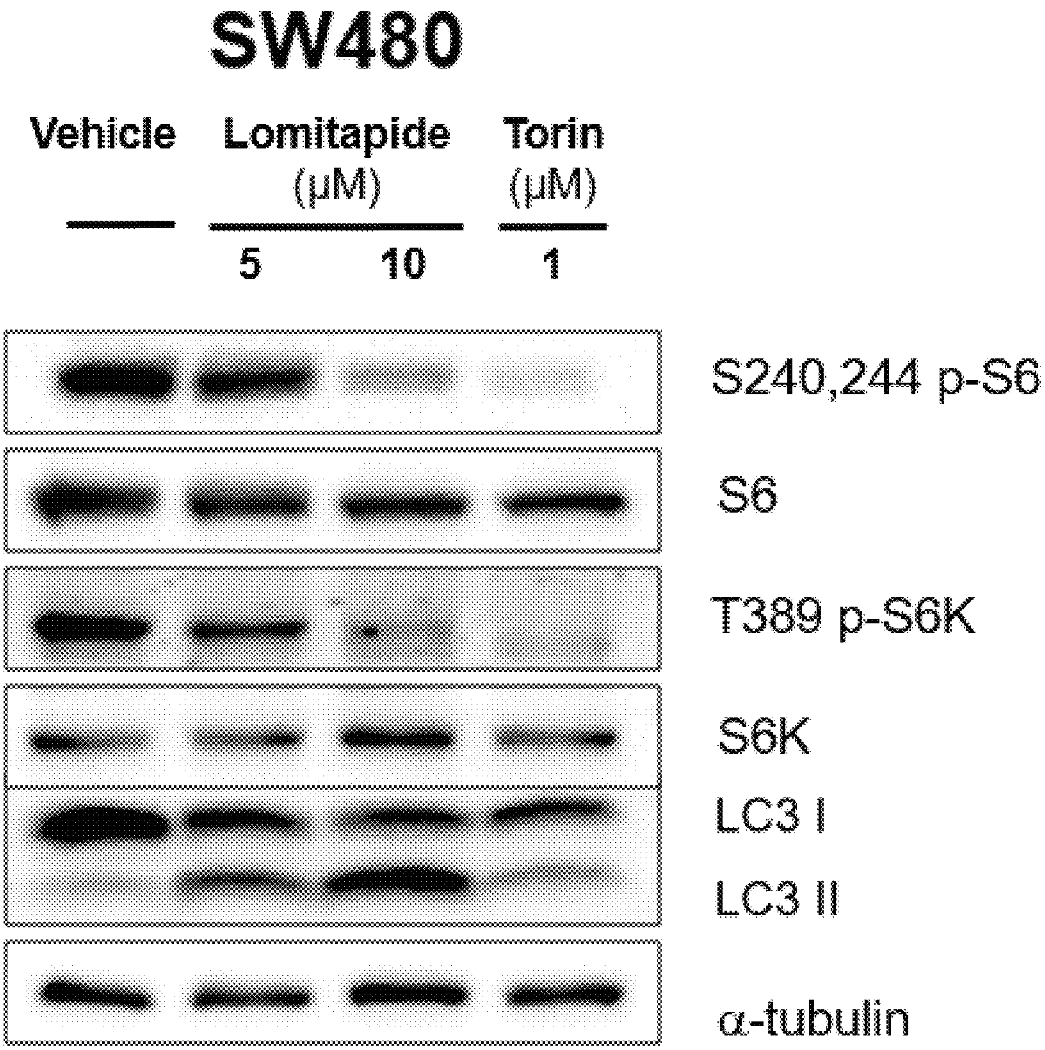
FIG. 7*a* shows western blotting analysis results of proteins related to mTOR signaling and autophagy for the colorectal cancer cell line SW480 after treatment with the control drug DMSO and lomitapide.
Figure 7B:
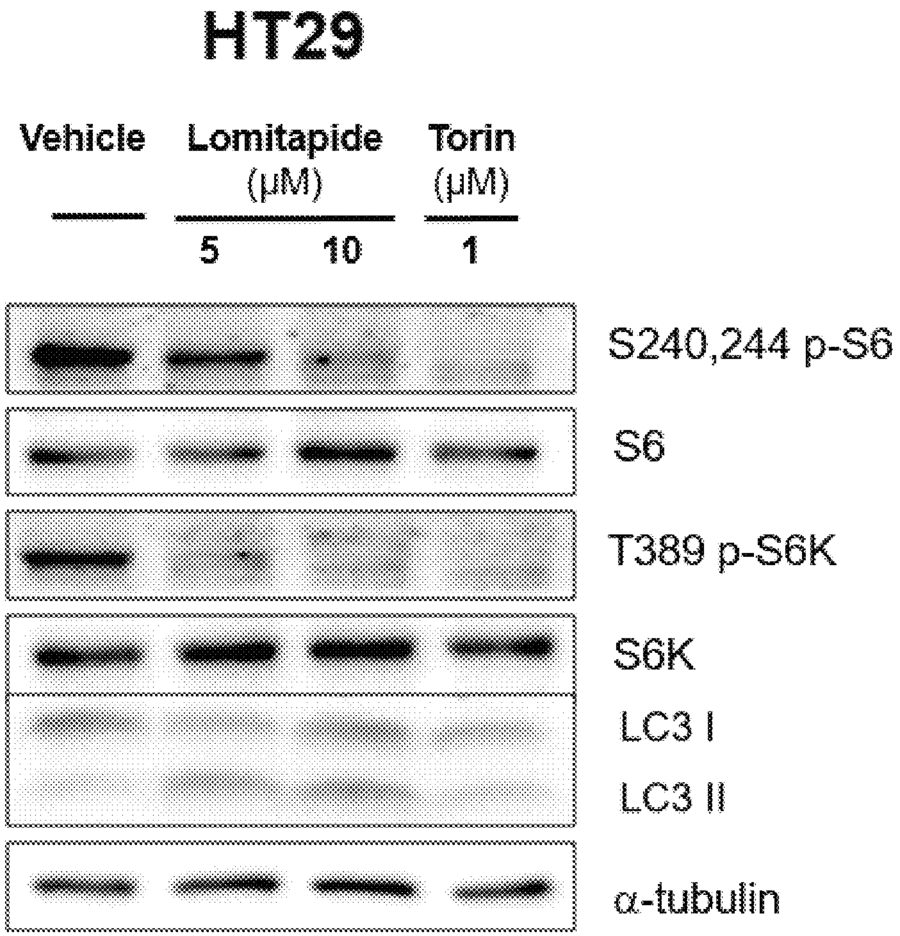
FIG. 7*b* shows western blotting analysis results of proteins related to mTOR signaling and autophagy for the colorectal cancer cell line HT29 after treatment with the control drug DMSO and lomitapide.
Figure 7C:
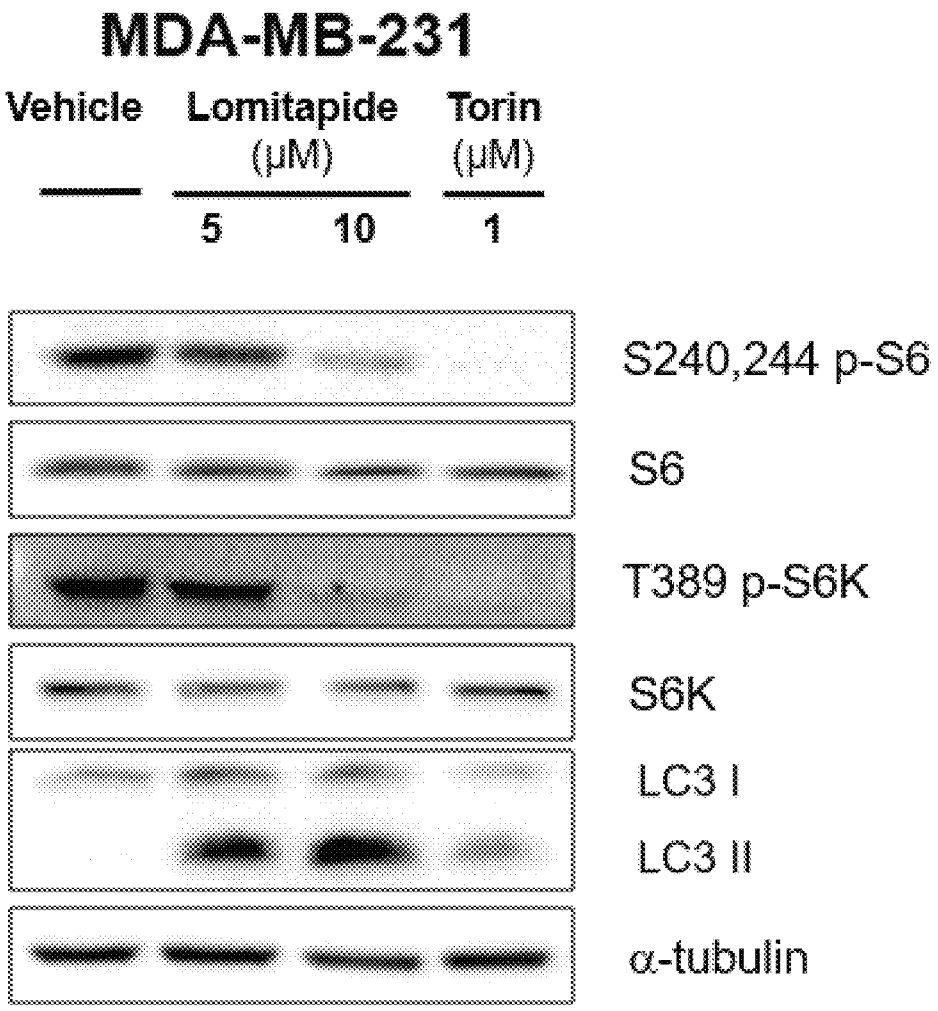
FIG. 7*c* shows western blotting analysis results of proteins related to mTOR signaling and autophagy for the breast cancer cell line MDA-MB-231 after treatment with the control drug DMSO and lomitapide.
Figure 7D:
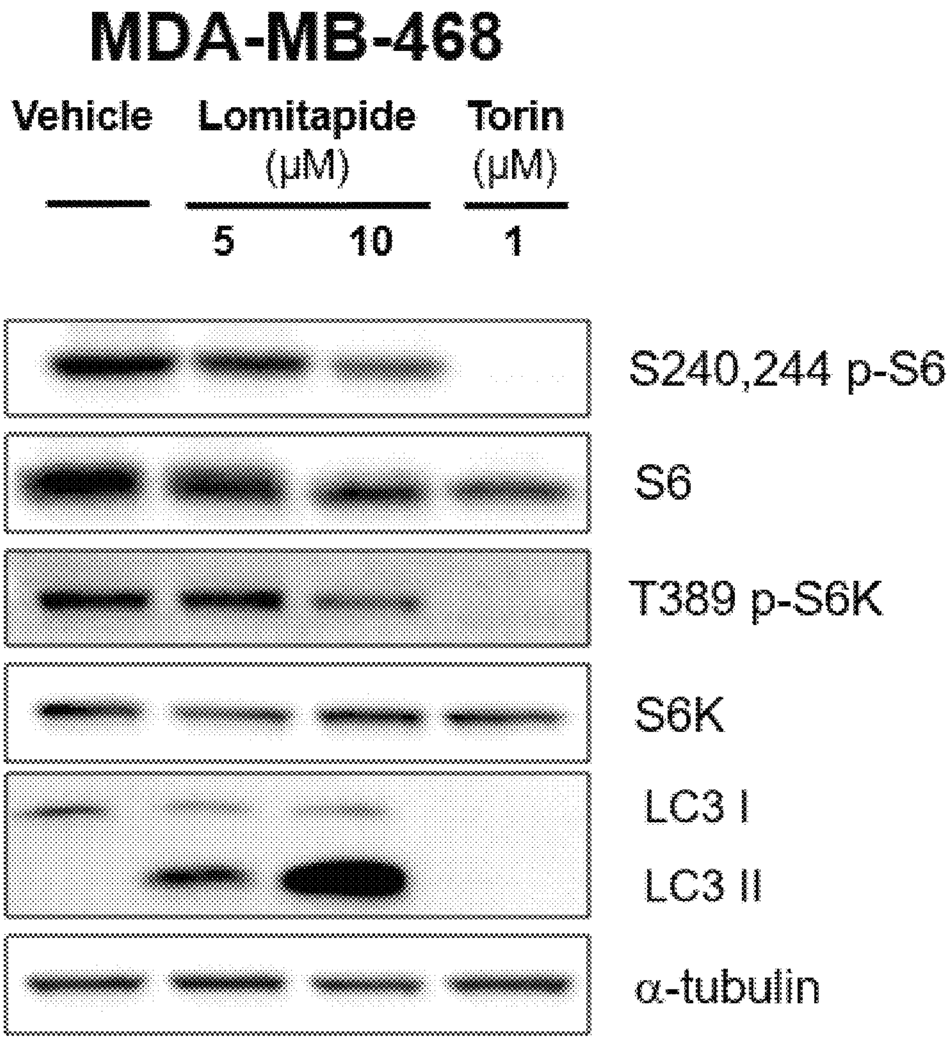
FIG. 7*d* shows western blotting analysis results of proteins related to mTOR signaling and autophagy for the breast cancer cell line MDA-MB-468 after treatment with the control drug DMSO and lomitapide.
Figure 7E:
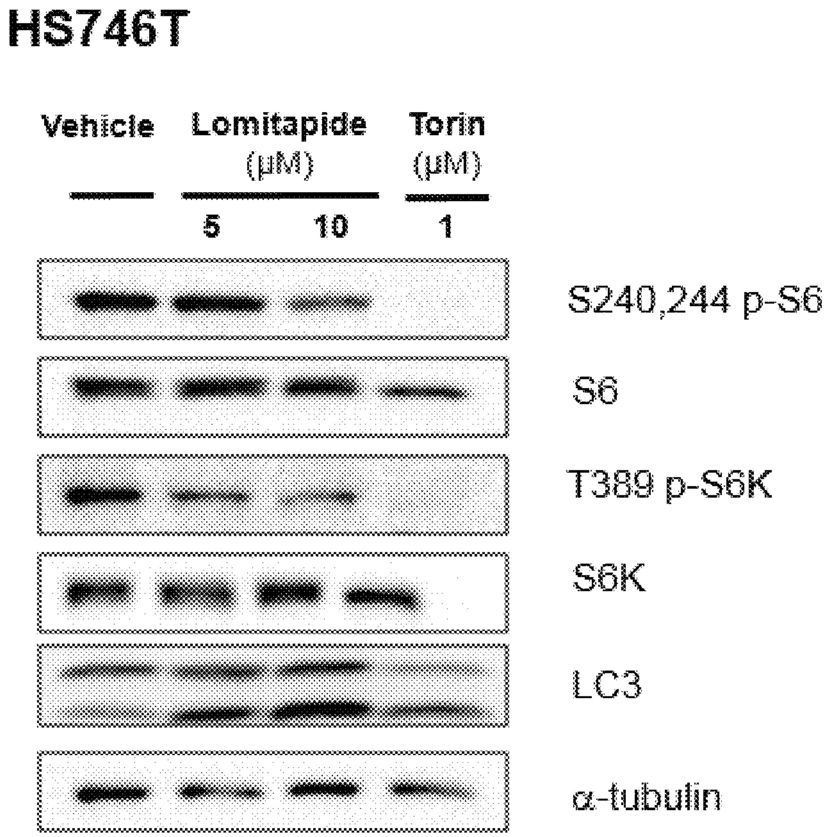
FIG. 7*e* shows western blotting analysis results of proteins related to mTOR signaling and autophagy for the stomach cancer cell line HS746T after treatment with the control drug DMSO and lomitapide.
Figure 7F:
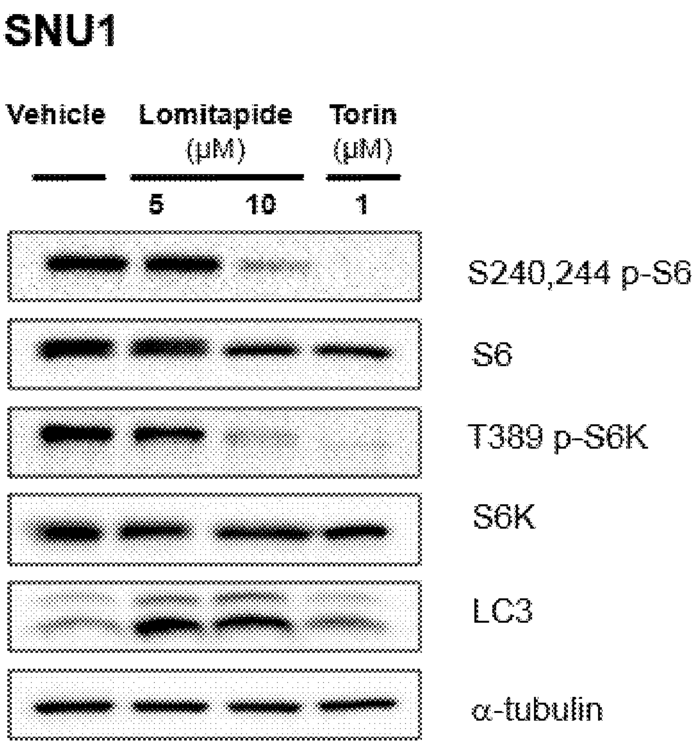
FIG. 7*f* shows western blotting analysis results of proteins related to mTOR signaling and autophagy for the stomach cancer cell line SNU1 after treatment with the control drug DMSO and lomitapide.
Figure 7G:
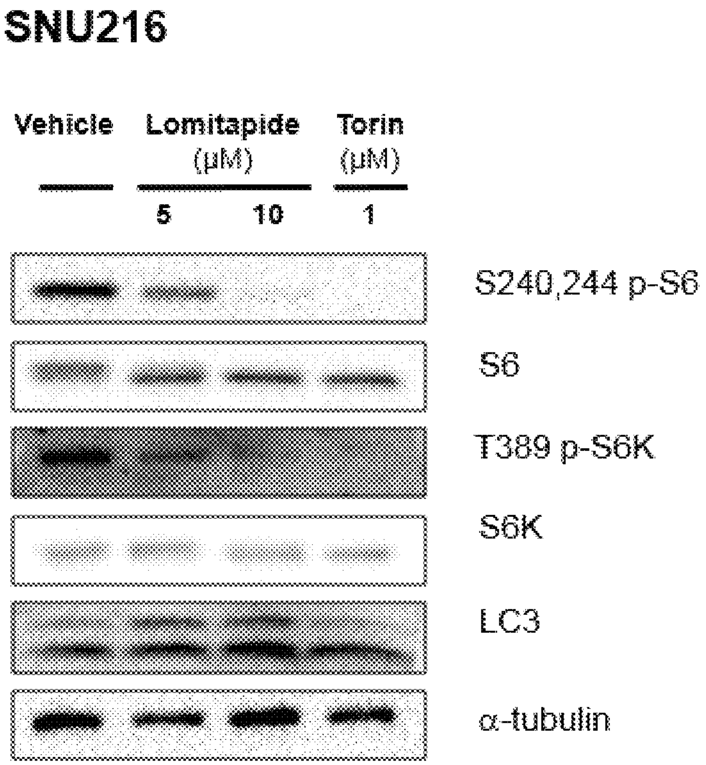
FIG. 7*g* shows western blotting analysis results of proteins related to mTOR signaling and autophagy for the stomach cancer cell line SNU216 after treatment with the control drug DMSO and lomitapide.

Through the experiments, it was identified that lomitapide remarkably decreased phosphorylation levels of target proteins (p-S6K, p-S6) in a dose-dependent manner and increased induction of conversion from LC3I into LC3II (FIGS. 7*e* to 7*g*). This result implies that lomitapide is highly effective for inhibiting mTOR and its upstream signaling pathway (AKT, p-S6K, and p-S6).

Example 4: Autophagy Assay for Lomitapide-Treated Cells

To confirm relationship lomitapide with cell autophagy function in HS746T cells, examination was made of cell signaling effects in the cells upon addition of lomitapide.

HCT116 cells treated with various concentration (0, 5, and 10 μM) of lomitapide were analyzed for change in cell autophagy-related cell signaling pathway by western blotting. To this end, the supernatant obtained in Example 3 was loaded onto 10% SDS-PAGE gel. The proteins thus separated were blotted onto a PVDF membrane. Then, the blots were incubated with anti-p-AMPK, anti-LC3, anti-p-ULK1 antibodies (Cell Signaling Technology, Massachusetts, USA) at 4° C. for 12 hours. Afterward, the blots were washed with TBST (a mixture of tris-buffered saline (TBS) and Tween 20), incubated with horseradish peroxidase-conjugated secondary antibody (Cell signaling) at 37° C. for 1 hour, and washed, followed by detecting enhanced chemiluminescence (ECL; Amersham).

Figure 8:
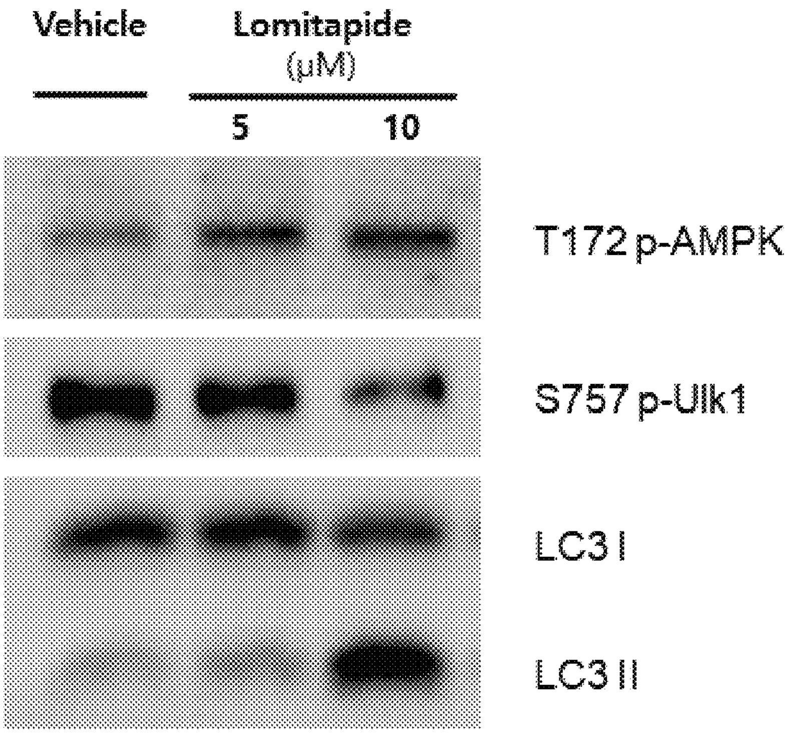
FIG. 8 shows western blotting analysis results of proteins related to cell autophagy for the colorectal cancer cell line HCT116 after treatment with the control drug DMSO and lomitapide.

Through the experiments, it was identified that lomitapide remarkably increased a phosphorylation level of AMPK target in a dose-dependent manner and significantly increased induction of conversion from LC3I into LC3II (FIG. 8). This result suggests that lomitapide greatly increased the expression of proteins involved in autophagy mechanism.

To confirm relationship lomitapide with cell autophagy function in HCT116 cells, examination was made of cell signaling effects and cell viability when the cells were treated with either or both of lomitapide and 3-methyladenine (3-MA, Sigma Aldrich, Missouri, USA), which is an inhibitor of autophagy.

For an assay for a change in cell autophagy-related cell signaling, HCT116 cells treated with either or both of 5 μM lomitapide and 1 mM 3-MA were subjected to western blotting. This western blot analysis was conducted in the same above-mentioned manner with the exception of using an anti-LC3 antibody.

For cell viability assay, HCT116 cells were seeded at a density of $10^4$ cells/well into 96-well plates and incubated 37° C. for 24 hours before treatment with either or both of 5 μM lomitapide and 1 mM 3-MA at 37° C. for 24 hours in a 5% $CO_2$ atmosphere. Thereafter, the cells in each well were added with 100 μL of an assay reagent (CellTiter-Glo® Reagent) and observed under a microscope.

Figure 9:
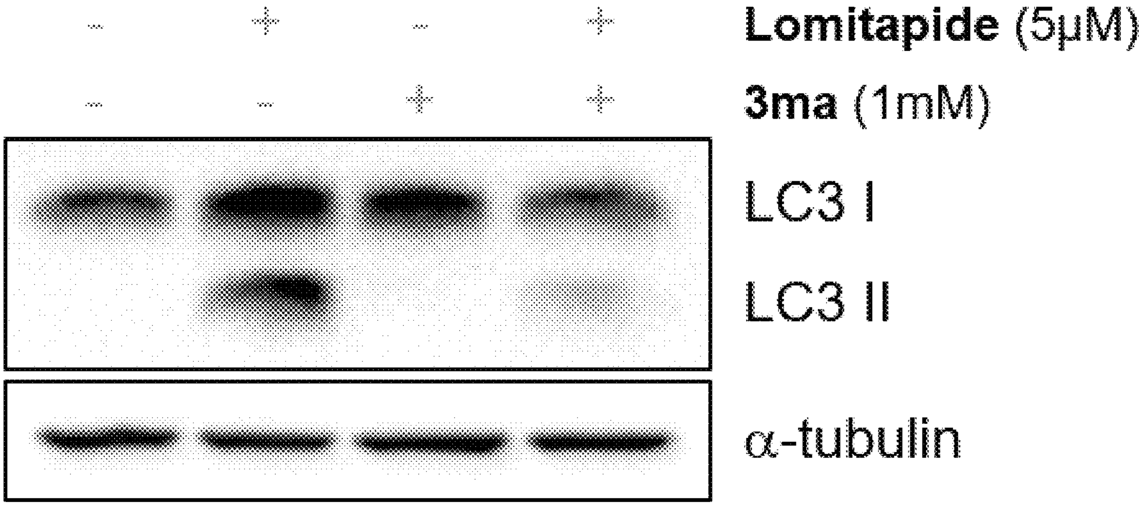
FIG. 9 shows western blotting analysis results of autophagy-induced cell death for the colorectal cancer cell line HCT116 after treatment with the control drug DMSO, 3-methyladenine (3-MA), and lomitapide.
Figure 10:
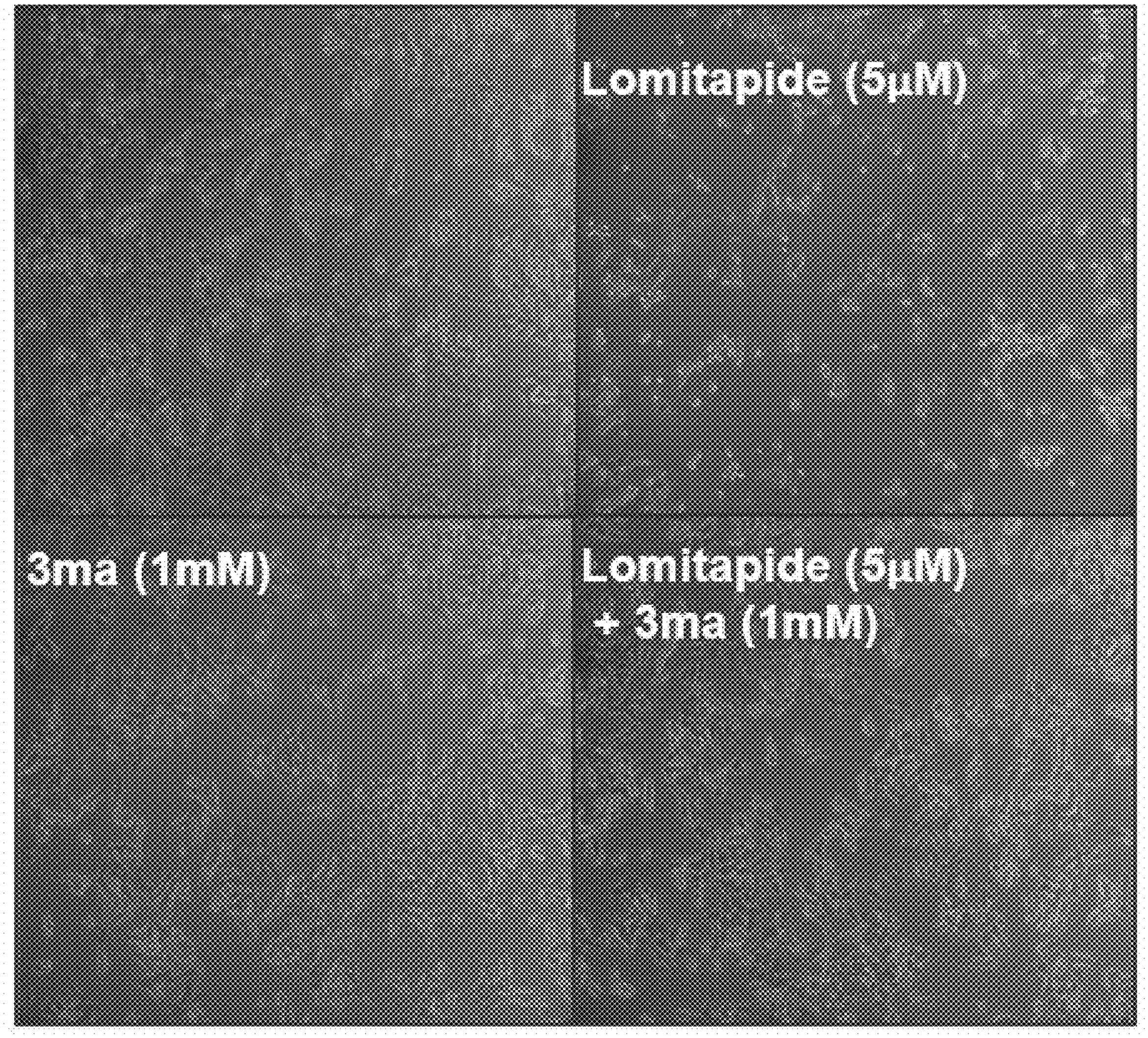
FIG. 10 shows microscopic images accounting for autophagy-induced cell death for the colorectal cancer cell line HCT116 after treatment with the control drug DMSO, lomitapide, and 3-methyladenine (3-MA).

Through the assay, it was discovered that the induction of conversion from LC3I into LC3II was significantly reduced in HCT116 cells treated with both lomitapide and 3-MA (FIG. 9). In addition, the cell viability assay revealed that the HCT116 cells treated with both lomitapide and 3-MA are unlikely to undergo death (FIG. 10).

The data exhibits that lomitapide according to the present disclosure suppresses the AMPK and mTOR signaling pathway, thereby upregulating the expressing of the cell autophagy mechanism proteins.

Example 5: Assay for Significant Gene Expression and Mechanism in Lomitapide-Treated Cells (RNA-Seq Assay)

To examine relationship between the drug mechanism of lomitapide and genes, significantly expressed genes obtained by an RNA-seq assay and related mechanisms were analyzed through the gene set enrichment analysis (GSEA) and the pathway enrichment analysis.

GSEA is an analytical method for extracting a significant gene-set that shows statistically significant differences in expression values of the two classes among various gene-set constructed based on biological traits.

For the final detection of significant gene-sets, gene annotation databases (KEGG pathway, Gene Ontology, etc.) with various biological information about genes were used to discover various gene-sets by grouping genes with specific functions among all the genes used in the RNA-seq experiment. Significant genes were determined with reference to a difference in expression values between the two classes within each gene-set, and statistically significant gene-set was finally detected based on the significant genes.

Figure 11:
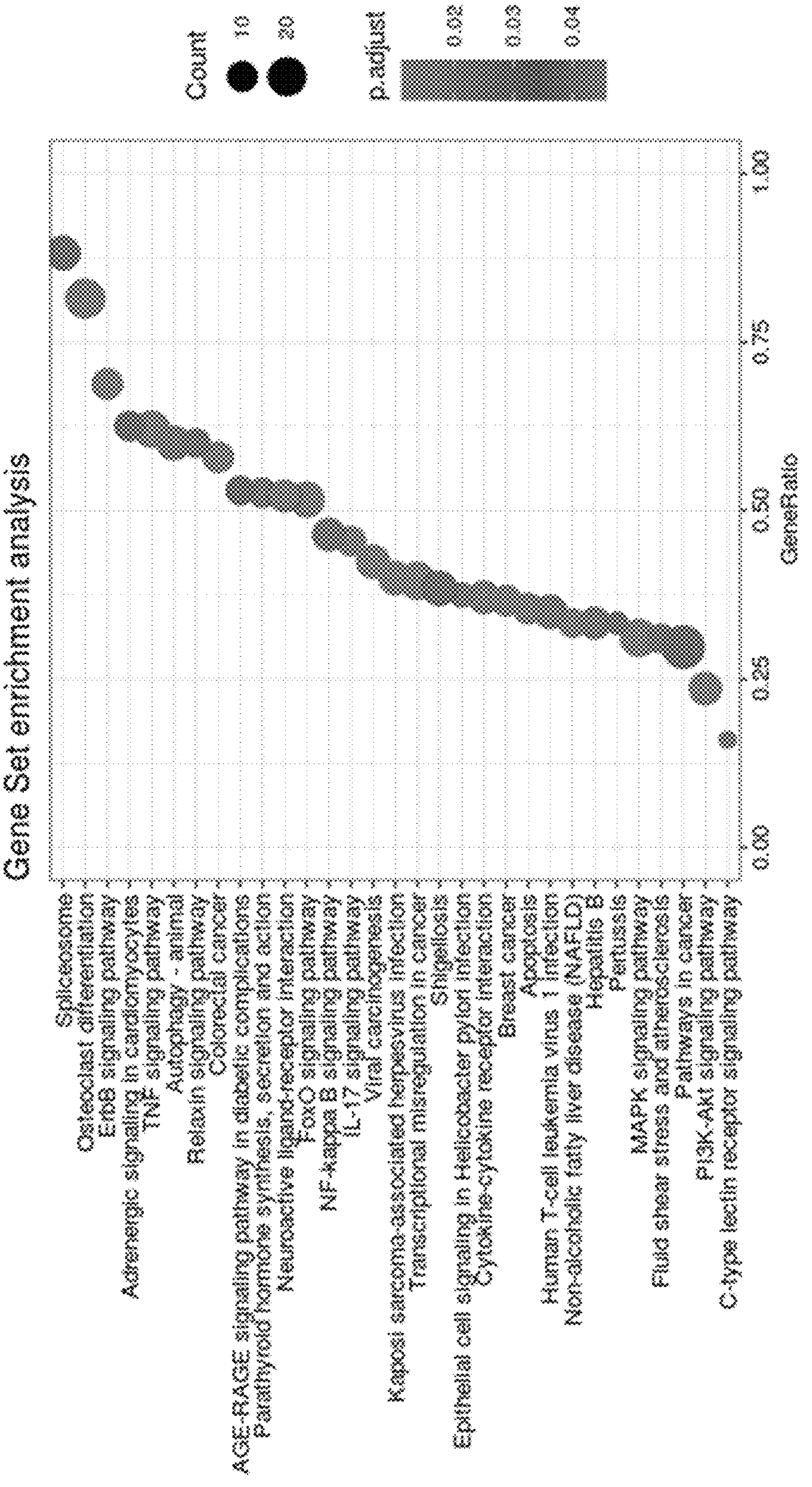
FIG. 11 shows RNA-seq assay results for significant gene-mechanism relationship in the colorectal cancer cell line HCT116 after treatment with the control drug DMSO and lomitapide.

As mechanisms belonging to a significant gene set, cancer-related mechanisms associated with the mTOR mechanism, including autophagy, were detected, along with mechanisms relating to immunity, senescence, and diabetes (FIG. 11 and Table 4).

TABLE 4

| No. | Gene Function | Gene Ratio | Related Disease |
|---|---|---|---|
| 1 | MAPK signaling pathway | 0.31 | Cancer |
| 2 | Kaposi sarcoma-associated herpesvirus infection | 0.4 | Cancer |
| 3 | Viral carcinogenesis | 0.42 | Cancer |
| 4 | Breast cancer | 0.37 | Breast cancer |
| 5 | FoxO signaling pathway | 0.52 | Cancer |
| 6 | Apoptosis | 0.35 | Cancer |
| 7 | TNF signaling pathway | 0.62 | Inflammation |
| 8 | Osteoclast differentiation | 0.81 | Osteoporosis |
| 9 | IL-17 signaling pathway | 0.45 | Inflammation, cancer |
| 10 | Colorectal cancer | 0.58 | Colorectal cancer |
| 11 | Transcriptional misregulation in cancer | 0.4 | Cancer |
| 12 | Hepatitis B | 0.33 | Inflammation, cancer |
| 13 | Non-alcoholic fatty liver disease (NAFLD) | 0.33 | Non-alcoholic hepatitis, hepatocirrhosis, and liver failure |
| 14 | Parathyroid hormone synthesis, secretion and action | 0.53 | Calcium metabolism, cancer |
| 15 | Adrenergic signaling in cardiomyocytes | 0.62 | Heart disease |
| 16 | Epithelial cell signaling in Helicobacter pylori infection | 0.38 | Gastritis, stomach cancer |
| 17 | Human T-cell leukemia virus 1 infection | 0.35 | Leukemia |
| 18 | Cytokine-cytokine receptor interaction | 0.37 | Inflammation, cancer |
| 19 | Autophagy - animal | 0.6 | Cancer, metabolic disease |
| 20 | C-type lectin receptor signaling pathway | 0.16 | Immunity, cancer |
| 21 | Spliceosome | 0.88 | — |
| 22 | Relaxin signaling pathway | 0.6 | Heart disease |
| 23 | AGE-RAGE signaling pathway in diabetic complications | 0.53 | Diabetic complications |
| 24 | Pertussis | 0.33 | Whooping cough |
| 25 | PI3K-Akt signaling pathway | 0.24 | Cancer |
| 26 | Fluid shear stress and atherosclerosis | 0.31 | Arteriosclerosis |
| 27 | ErbB signaling pathway | 0.69 | Cancer |
| 28 | NF-kappa B signaling pathway | 0.46 | Inflammation, cancer |
| 29 | Pathways in cancer | 0.3 | Cancer |
| 30 | Neuroactive ligand-receptor interaction | 0.52 | — |
| 31 | Endocrine resistance | 0.41 | Metabolic disease |
| 32 | Signaling pathways regulating pluripotency of stem cells | 0.39 | Cancer |
| 33 | Peroxisome | 0.83 | — |
| 34 | Protein processing in endoplasmic reticulum | 0.26 | — |
| 35 | Shigellosis | 0.38 | Bacillary dysentery |

Figure 12:
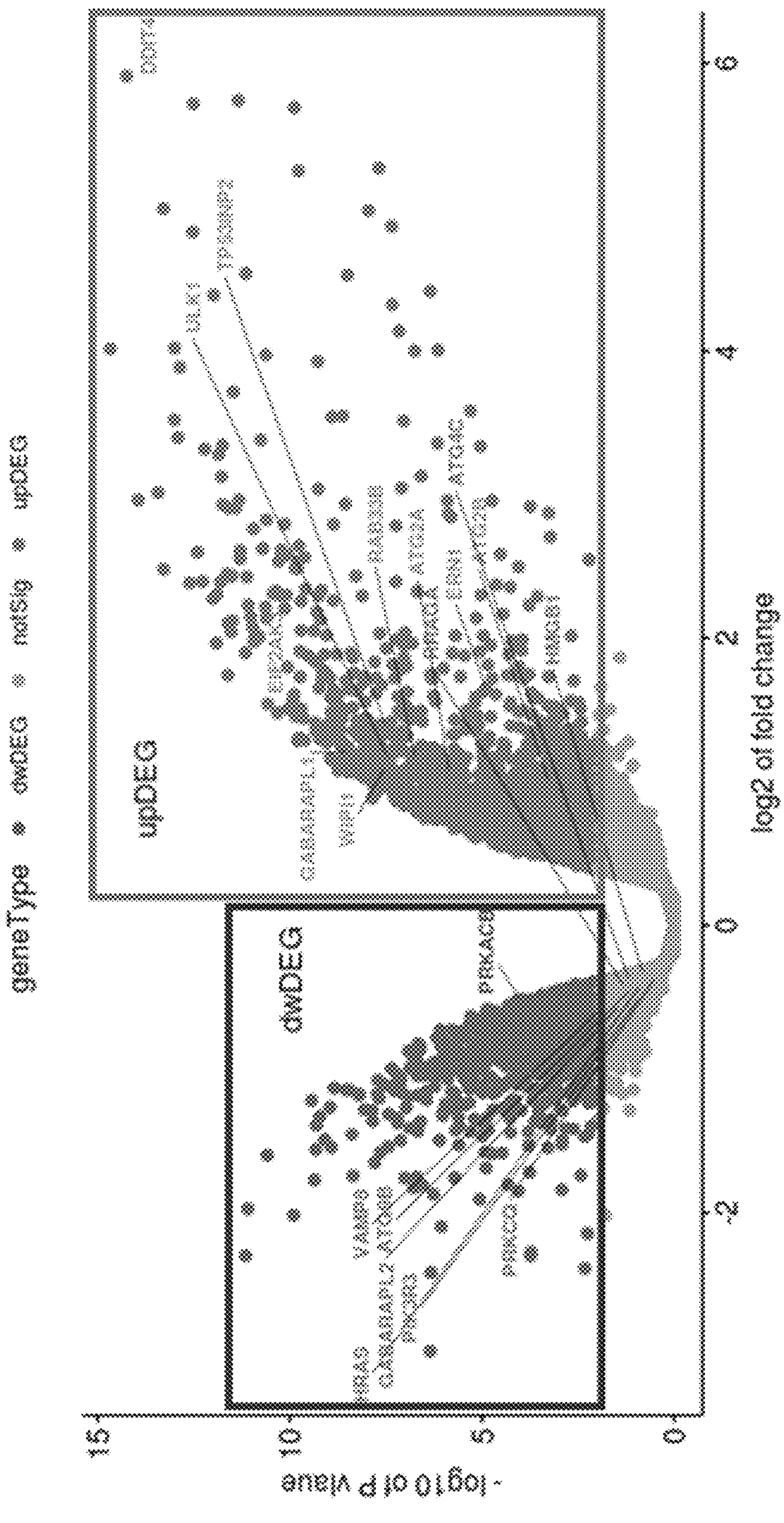
FIG. 12 shows RNA-seq assay results for autophagy-related significant genes in the colorectal cancer cell line HCT116 after treatment with the control drug DMSO and lomitapide.

In addition, autophagy mechanism-related significant gene analysis (Differentially Expressed Genes analysis, DEG analysis) revealed that the autophagy-related genes ATG family, ULK1, and DDIT4 were significantly expressed (FIG. 12). In DEG analysis, expression values of genes are measured and statistically processed to select a significant gene candidate group (differentially expression genes) with a difference in expression between a control and a comparison group.

As understood from the data, the effect of lomitapide on cancer cells is implemented through i) inhibition of the mTOR signaling pathway and ii) expression of autophagy-related genes.

Example 6: Cell Colony Forming Assay for Lomitapide-Treated Cells

To examine relationship between lomitapide and cancer cell colony forming rate in HCT116 cells, cancer cell colony forming rates were measured after addition of limitapide to HCT116 cells cultured in wells.

HCT116 cells were seeded at a density of $10^5$ cells/well into 12-well plates and incubated 37° C. for 24 hours. Subsequently, the cells were incubated with 0 and 5 μM lomitapide at 37° C. for 48 hours in a 5% $CO_2$ atmosphere. Then, 500 μL of crystal violet was added to each well and incubated at room temperature for 10 minutes to stain the cells. From the staining data, the cells were analyzed for growth rate.

Figure 13:
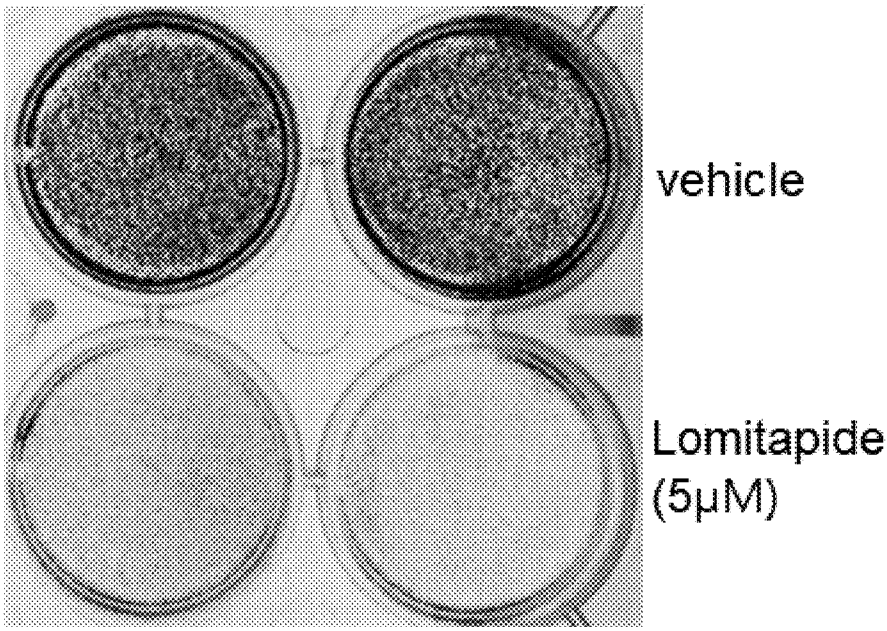
FIG. 13 shows colony formation of the colorectal cancer cell line HCT116 after treatment with the control drug DMSO and lomitapide.

In this assay, the cells in wells treated with lomitapide were observed to be remarkably lower in growth rate than those in wells treated without lomitapide (FIG. 13).

This result indicates that lomitapide has an excellent anticancer effect.

Example 7: Anticancer Assay of Lomitapide Through Animal Experiment

Lomitapide was examined for anticancer effect in tumor-implanted mice by monitoring tumor sizes in the mouse xenograft model after treatment with lomitapide.

Figure 14A:
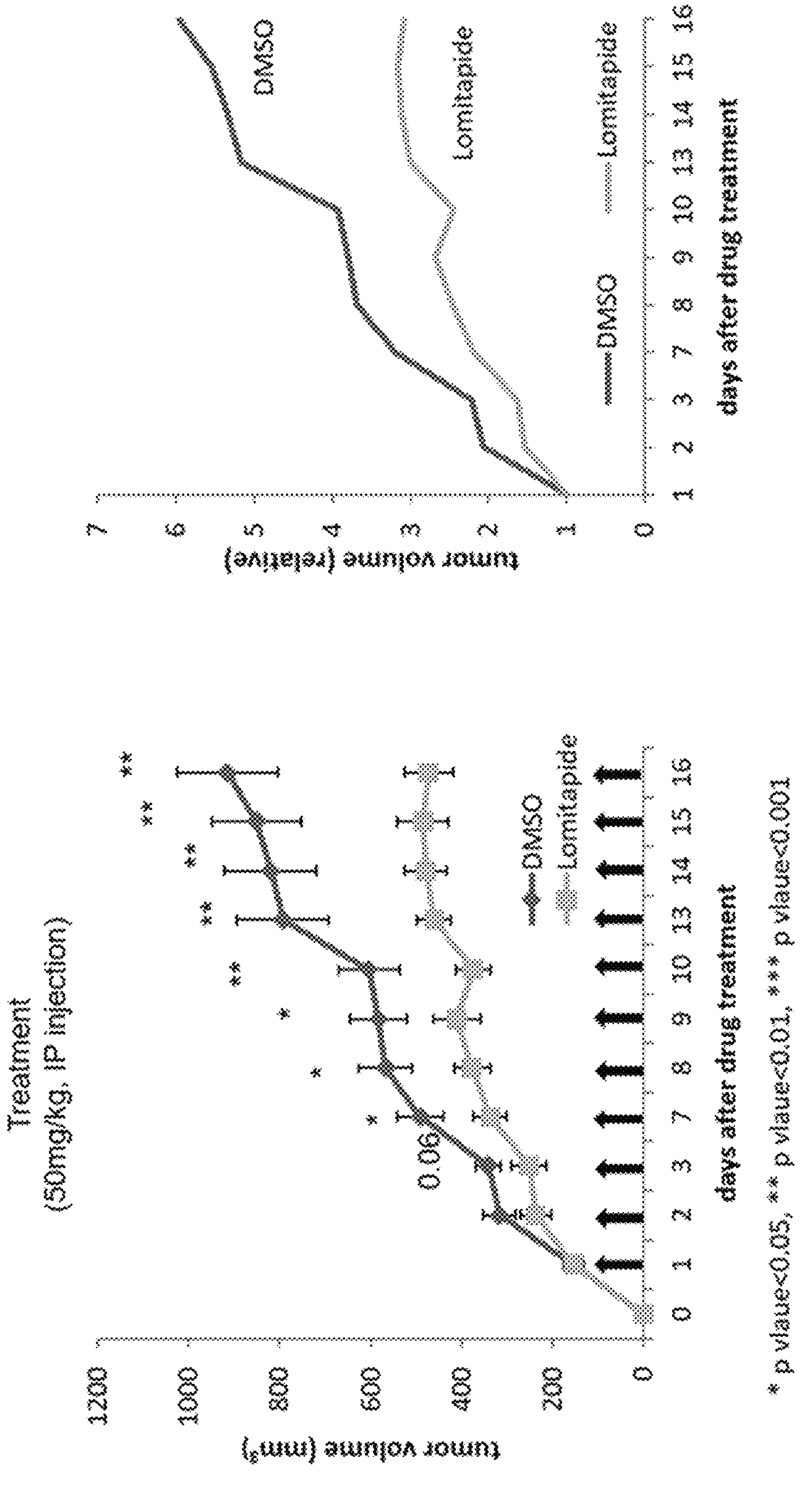
FIG. 14*a* shows plots of tumor sizes with time after treatment of colorectal cell line HCT116 xenografted into mice with the control and lomitapide (50 mg/Kg).

Animal experiments were conducted according to the guideline approved by the institutional animal care and use committee in the Korean Advanced Institute of Science and Technology. HCT116 cells ($4\times10^6$) were injected subcutaneously into male BALB/c nude mice at 8-12 weeks of age. After an average tumor volume reached 50 $mm^3$, the mice were randomly divided into two groups (5 mice/group). The mice were measured for weight and tumor size every two days. Tumor sizes were measured using calipers and determined according to formula $0.5\times(\text{width})^2\times(\text{Length})$. P-values were determined using Student's T test. Lomitapide was intraperitoneally injected at a dose of 50 mg/kg into the mice at days 1, 2, 3, 7, 8, 9, 13, 14, 15, and 16 after start of the experiment. For a control, DMSO was injected intraperitoneally into the mice (FIG. 14*a*).

Figure 14B:
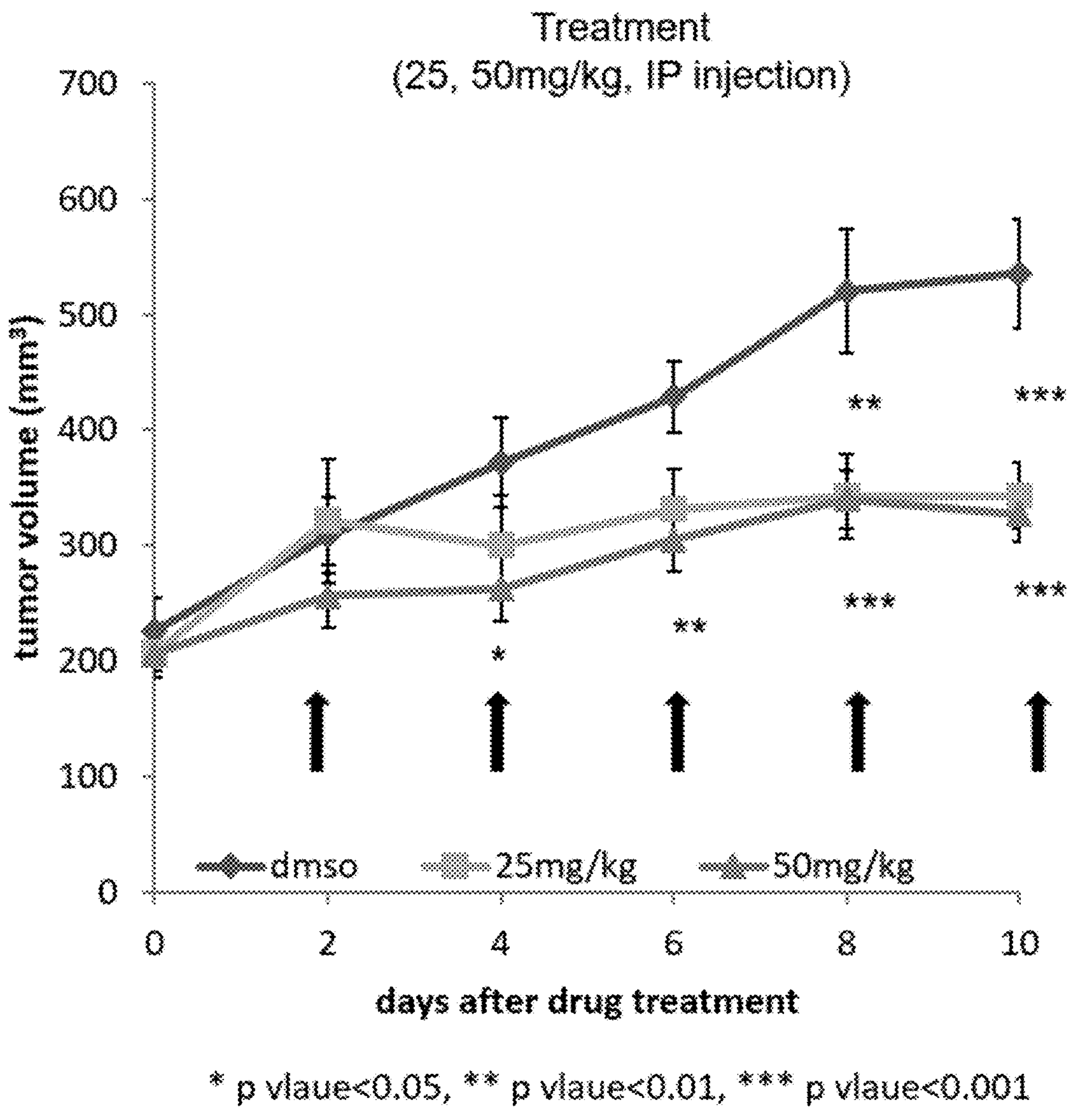
FIG. 14*b* shows plots of tumor sizes with time after treatment of colorectal cell line HCT116 xenografted into mice with the control and lomitapide (25 and 50 mg/Kg).

An additional animal experiment was conducted. Lomitapide was intraperitoneally injected at a dose of 25 or 50 mg/kg into mice five times every two days after start of the experiment. Intraperitoneal injection of DMSO into mice was conducted for a control (FIG. 14*b*).

Figure 14C:
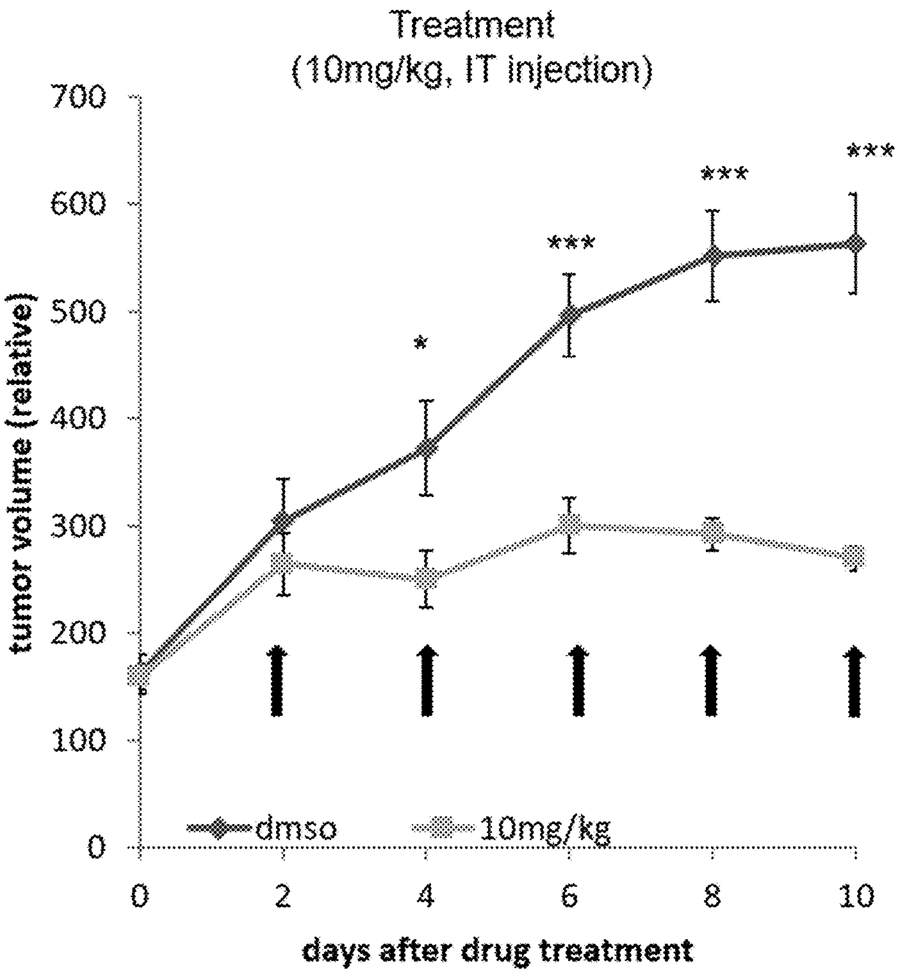
FIG. 14*c* is a plot of tumor sizes with time after treatment of colorectal cell line HCT116 xenografted into mice with the control and lomitapide (10 mg/Kg).
Figure 15A:
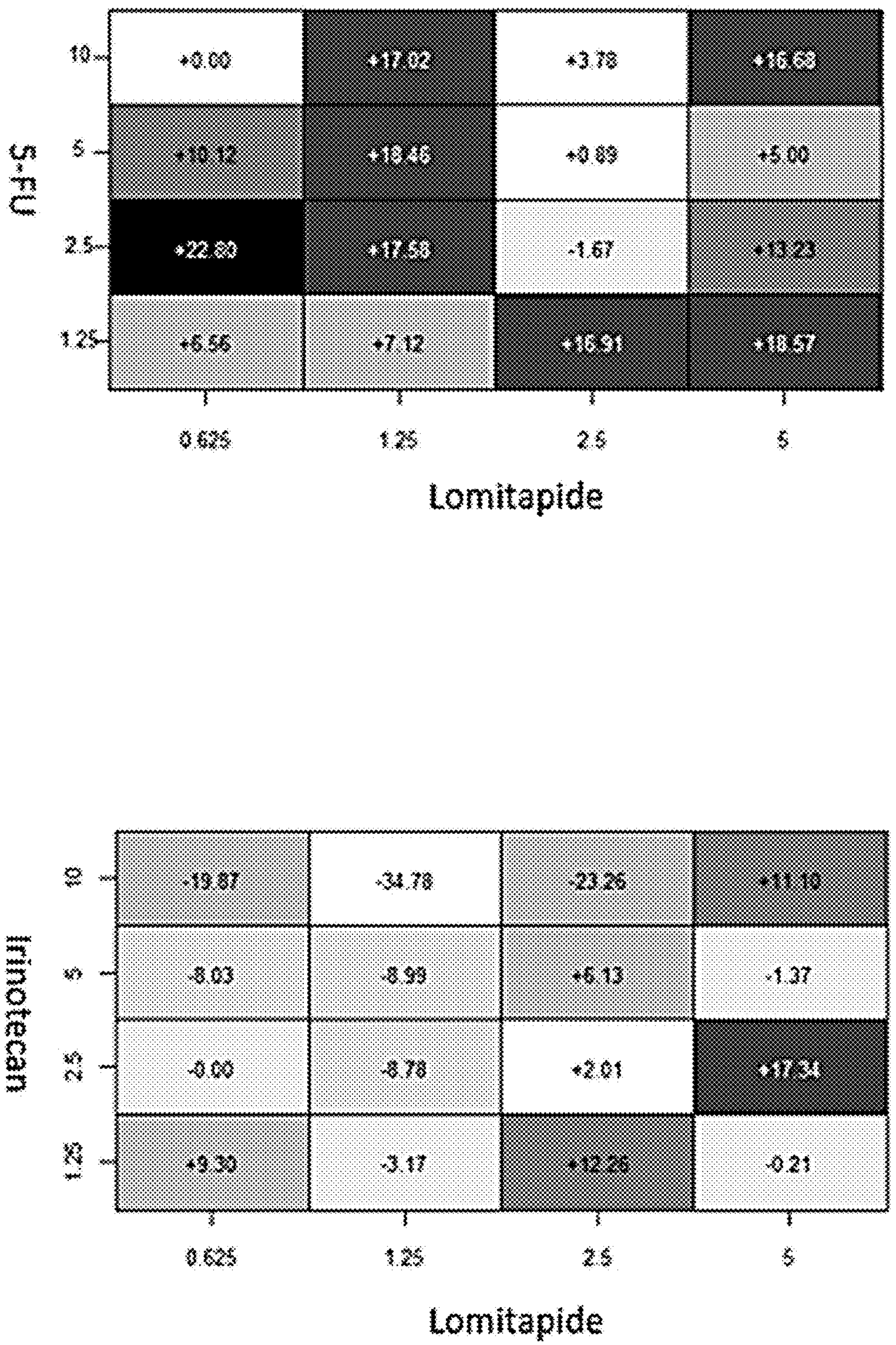
FIG. 15*a* shows analysis results of synergistic efficacy of 5-FU or irinotecan and lomitapide for the colorectal cancer cell line HCT116.
Figure 15B:
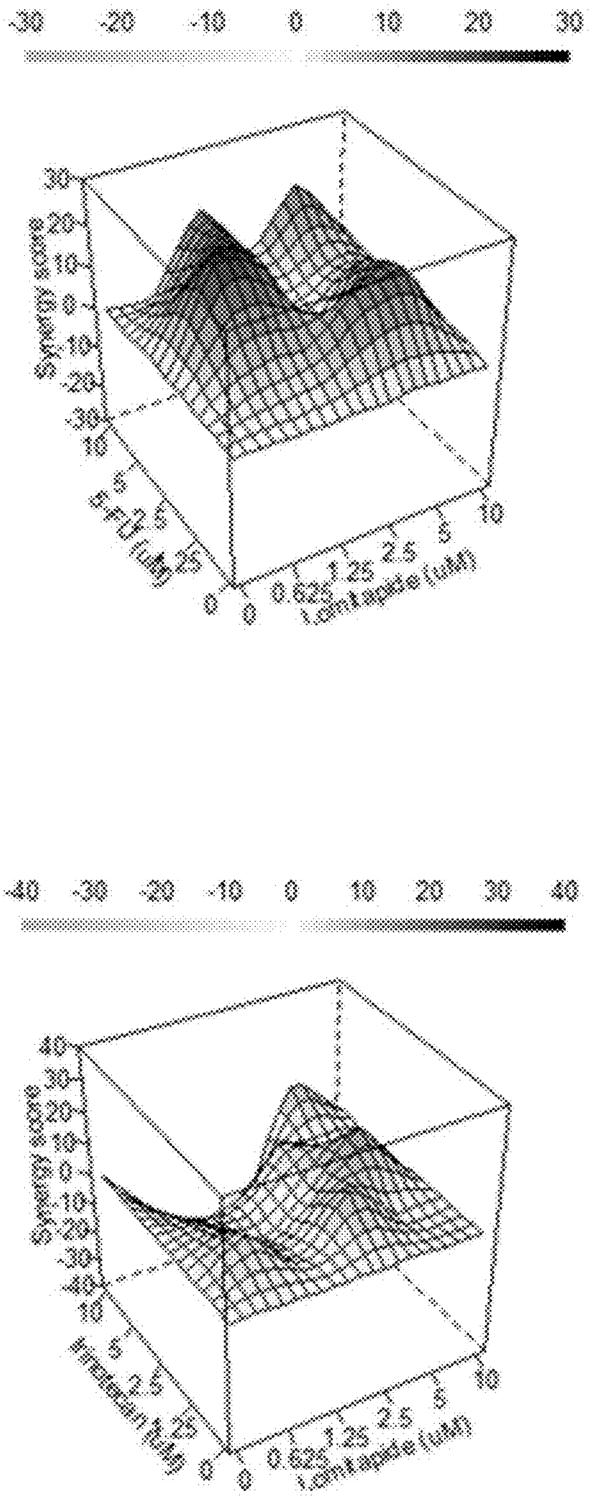
FIG. 15*b* shows analysis results of synergistic efficacy of 5-FU or irinotecan and lomitapide for the colorectal cancer cell line HCT116.
Figure 15C:
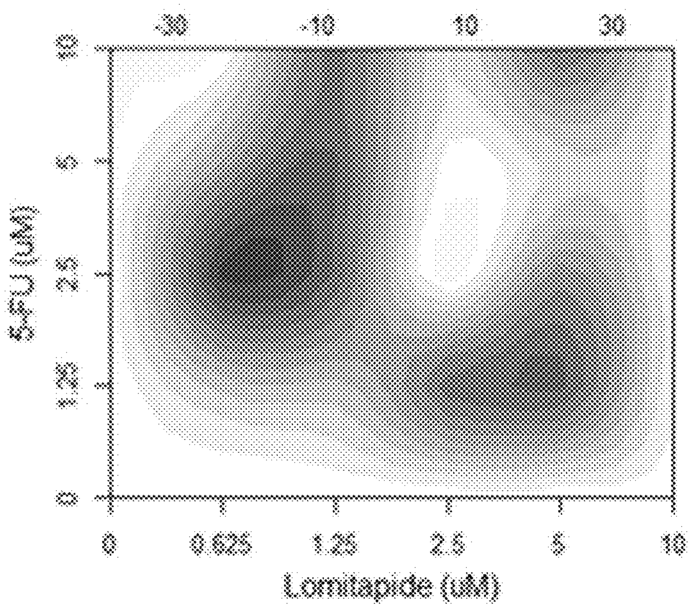
FIG. 15*c* shows analysis results of synergistic efficacy of 5-FU or irinotecan and lomitapide for the colorectal cancer cell line HCT116.
Figure 15C:
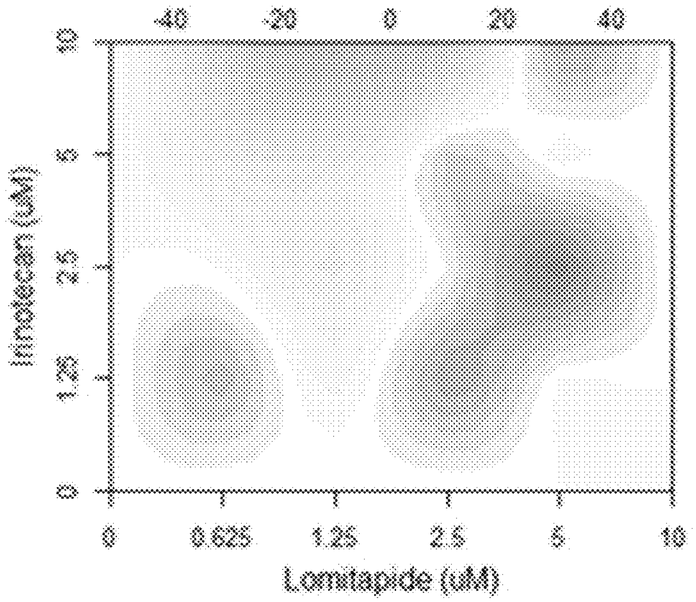
Figure 16A:
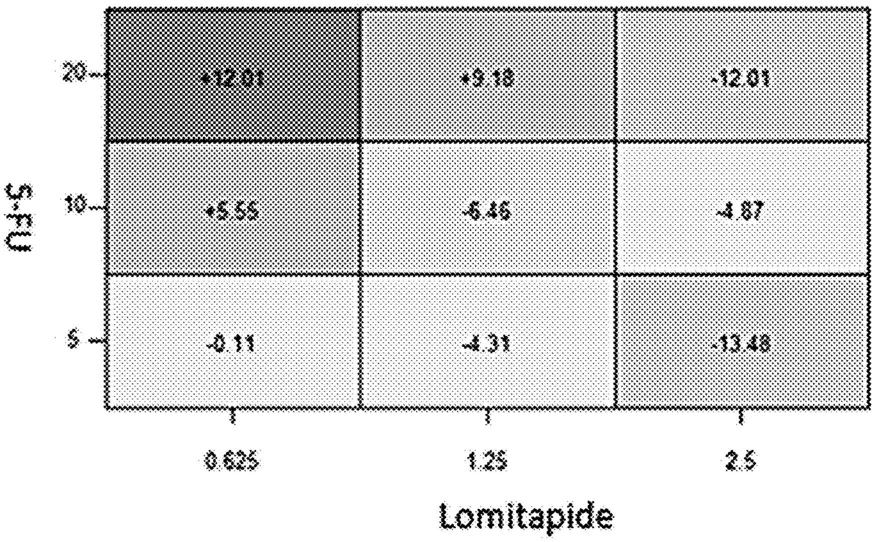
FIG. 16*a* shows analysis results of synergistic efficacy of 5-FU or irinotecan and lomitapide for the colorectal cancer cell line HT29.
Figure 16A:
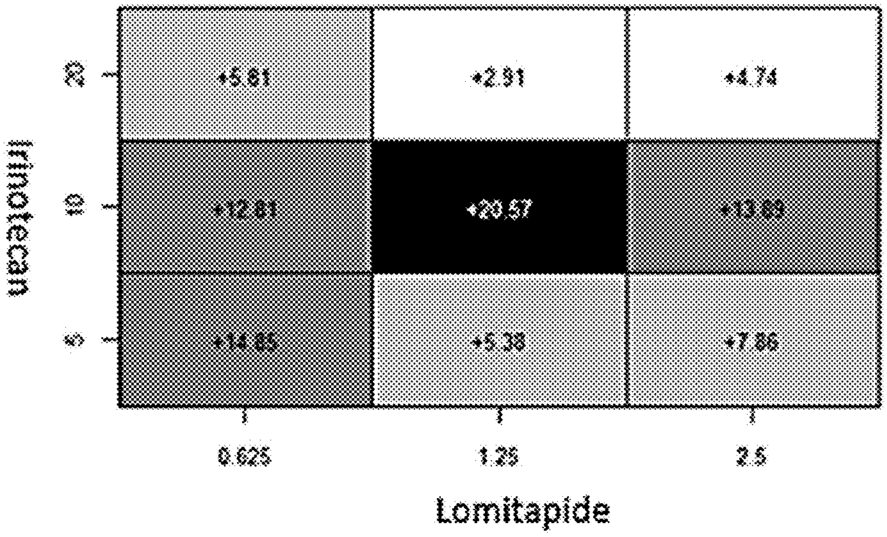
Figure 16B:
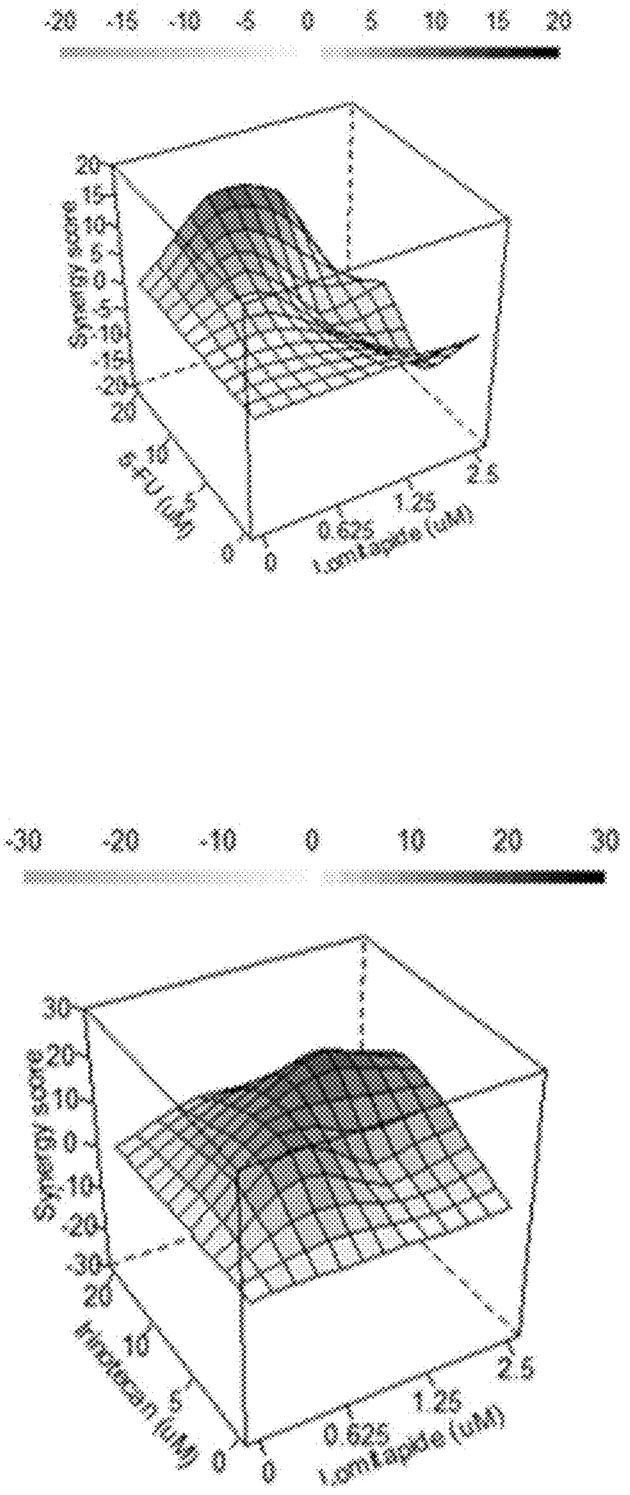
FIG. 16*b* shows analysis results of synergistic efficacy of 5-FU or irinotecan and lomitapide for the colorectal cancer cell line HT29.
Figure 16C:
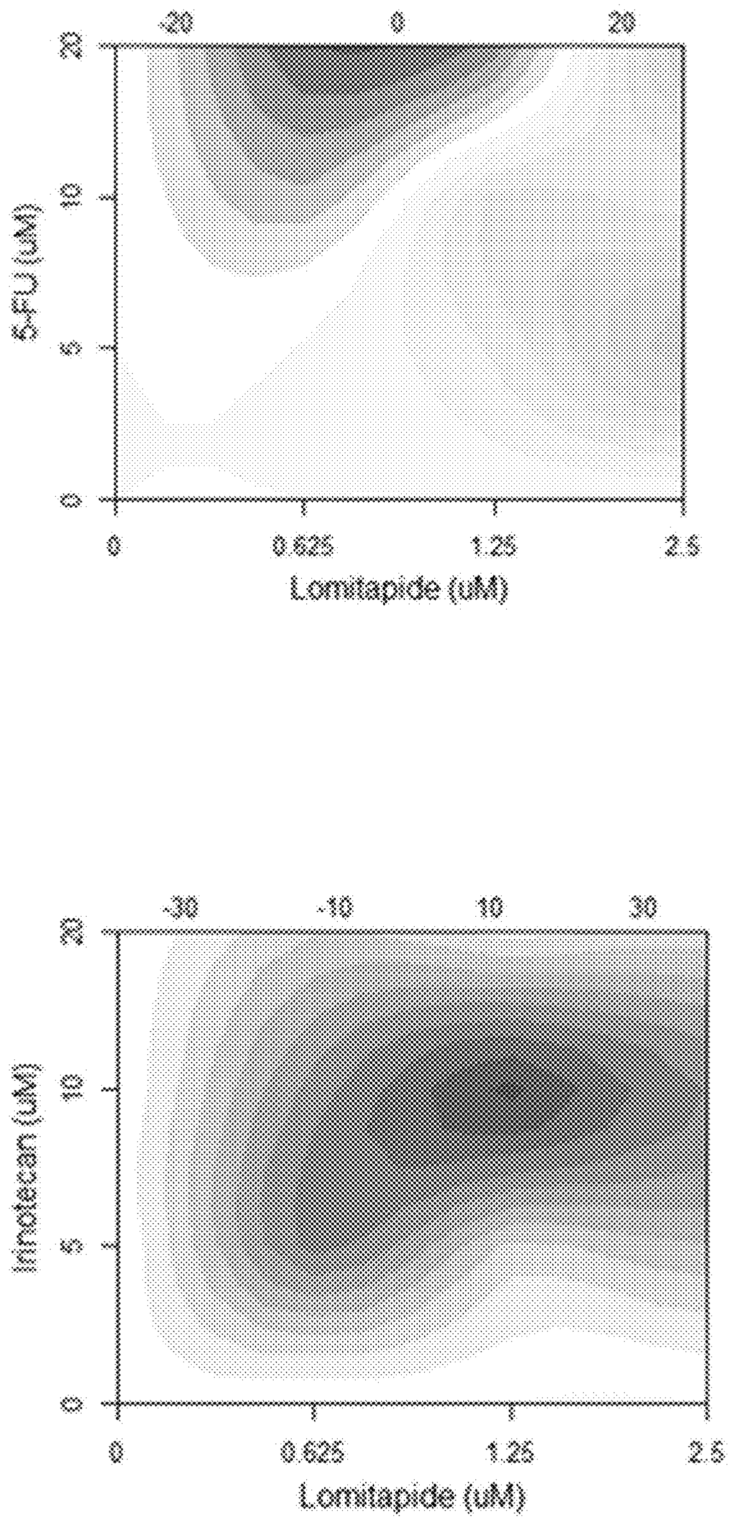
FIG. 16*c* shows analysis results of synergistic efficacy of 5-FU or irinotecan and lomitapide for the colorectal cancer cell line HT29.

In another additional animal experiment, lomitapide was intratumorally injected at a dose of 10 mg/kg into mice five times every two days after start of the experiment. Intratumoral injection of DMSO was conducted for a control (FIG. 14*c*).

In these experiments, tumors in the lomitapide-treated mouse xenograft model were observed to grow slowly, compared to the control (FIG. 14).

The data demonstrate an excellent anticancer effect of lomitapide.

Example 8: Assay for Drug Synergy According to Combination of Anticancer Drugs

HCT116, HT29, and SW480 cells were seeded into 96-well plates and treated with or without predetermined concentrations of individual drugs alone or in combination for 48 hours. In each well, DMSO was used at a final concentration of <0.01%. The concentrations used were observed to be free of toxicity. For assay, the following drugs were employed.

TABLE 5

| Drug | Manufacturer and Cat. No. |
|---|---|
| Lomitapide | Sellekchem, S7635 |
| 5-FU | Sigma Aldrich, F6627-1G |
| Irinotecan | Sellekchem, S2217 |

HCT116 cells were seeded at a density of 10,000 cells/well, and HT29 and SW480 cells were each seeded at a density of 5,000 cells/well. After incubation for 48 hours, 100 μL of an assay reagent (CellTiter-Glo® Reagent) was added to each well. Luminescence was read using VICTOR X Multilabel Reader (PerkinElmer, Massachusetts, USA) and used to calculate cell viability (%).

Drug synergy was evaluated using an HSA model. HSA scores were divided into three ranges of >10, −10~10, and <−10, which account for synergistic, additive, and antagonistic efficacies, respectively. Scores were given as individual points in each column of 4×4, 3×3, and 2×7 matrices of drug doses, and distributions of overall drug responses are depicted in two- and three-dimensional contour graphs.

Figure 17A:
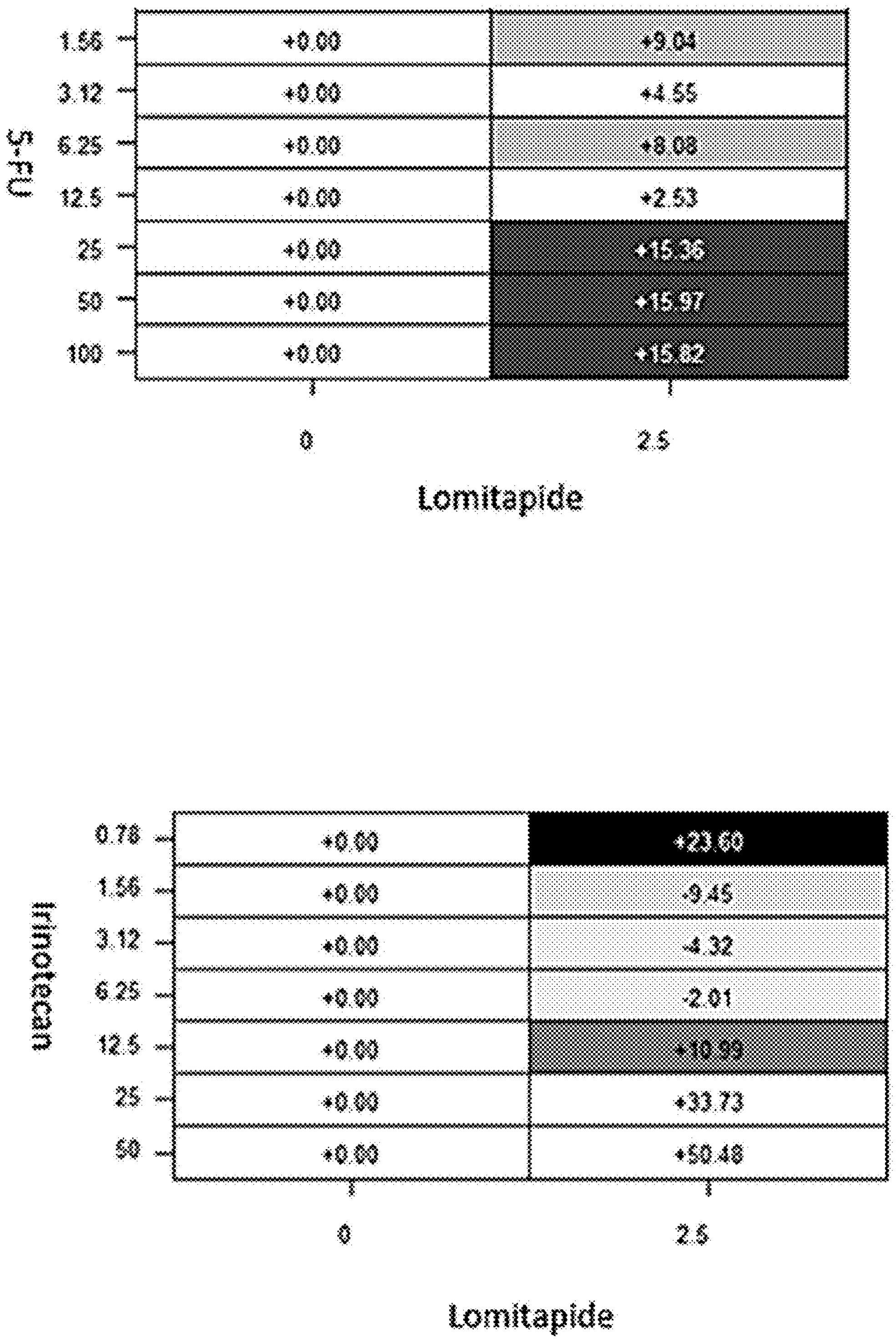
FIG. 17*a* shows analysis results of synergistic efficacy of 5-FU or irinotecan and lomitapide for the colorectal cancer cell line SW480.
Figure 17B:
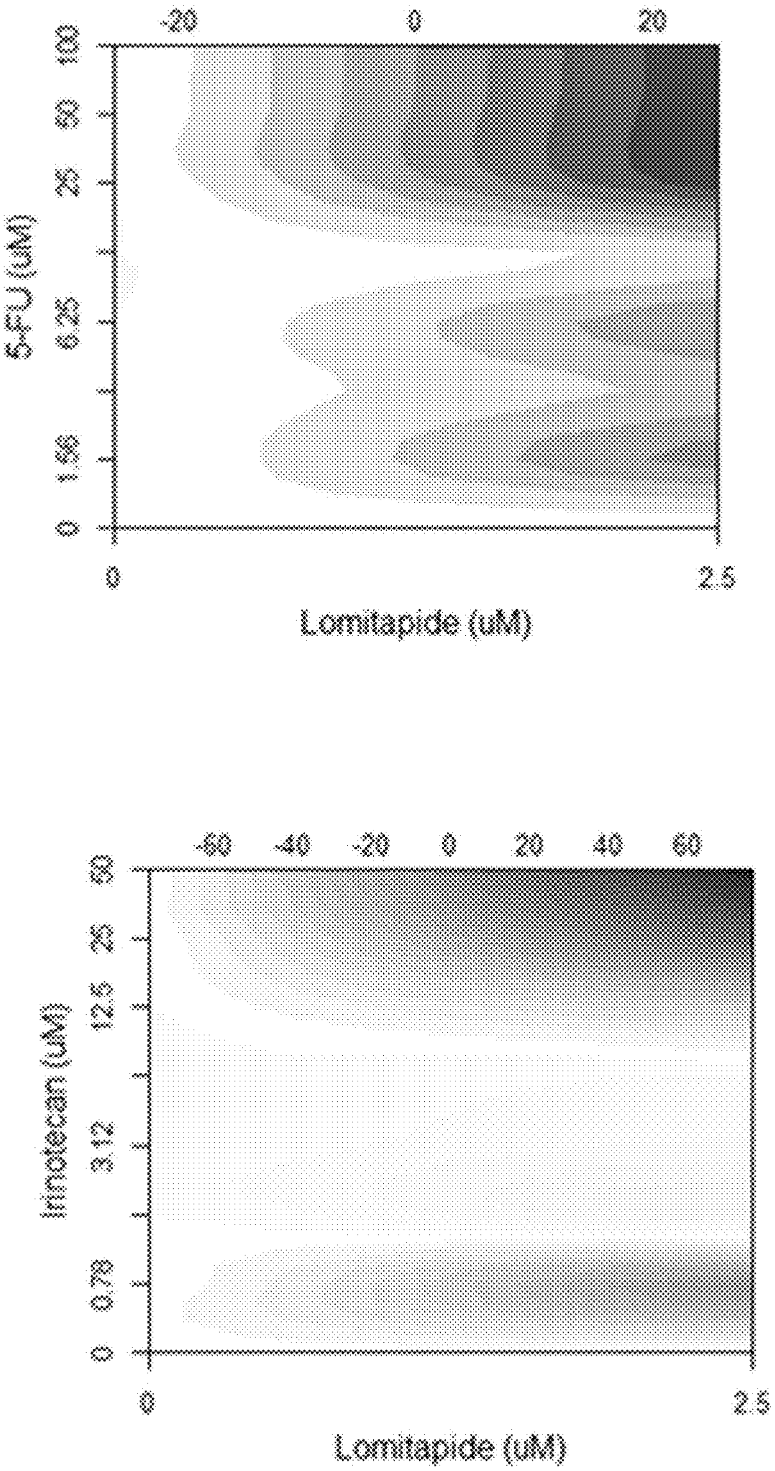
FIG. 17*b* shows analysis results of synergistic efficacy of 5-FU or irinotecan and lomitapide for the colorectal cancer cell line SW480.
Figure 17C:
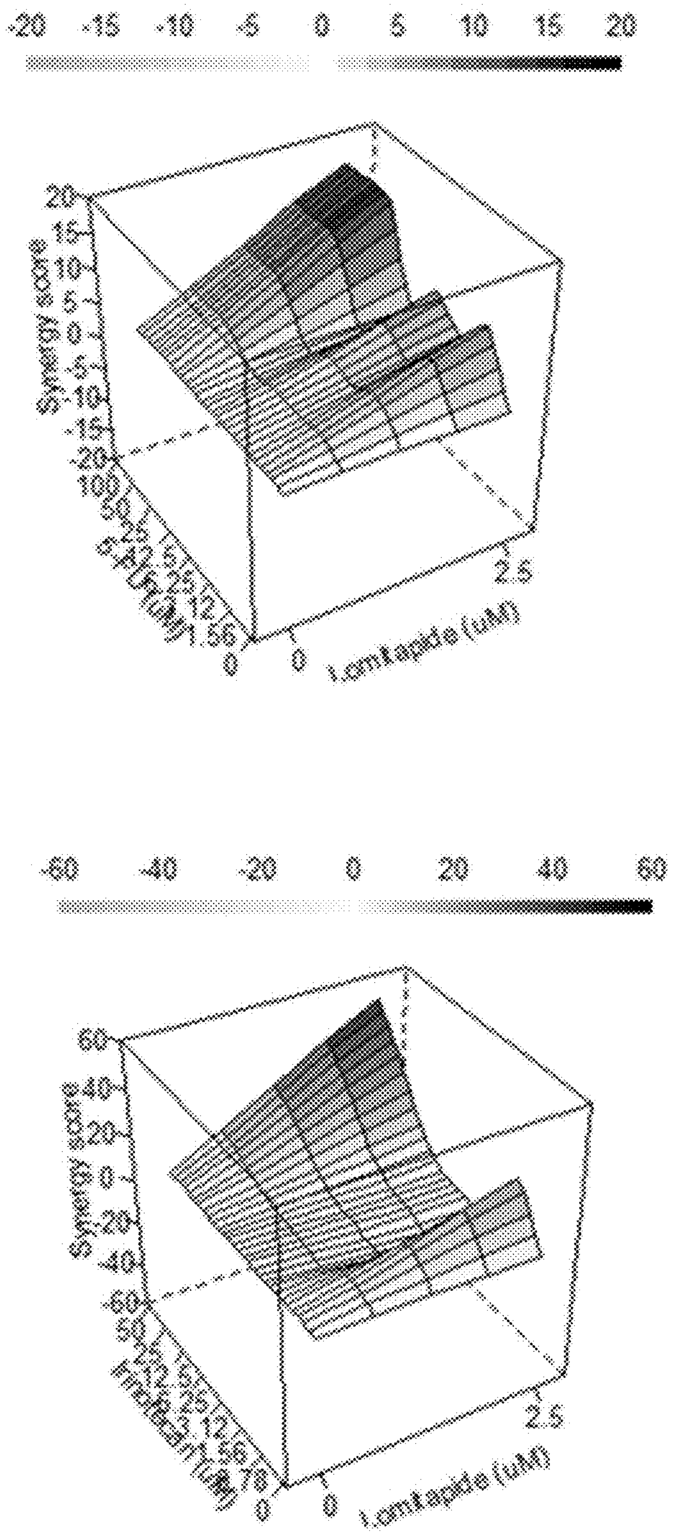
FIG. 17*c* shows analysis results of synergistic efficacy of 5-FU or irinotecan and lomitapide for the colorectal cancer cell line SW480.

In this assay, it was observed that synergic effects were obtained when lomitapide was used in combination with a conventional colorectal cancer drug, that is, 5-FU or irinotecan (FIGS. 15 to 17).

Example 9: Animal Test Analysis for Synergic Effect of Combined Use of Lomitapide and Anti-PD For mouse homograft tumor model, experiments were conducted using female C57B6/N mice (wild-type, 6 weeks old) with MC38 colorectal cancer and B16F10 melanoma cell lines. MC38 colorectal cancer and B16F10 melanoma cell lines were each subcutaneously injected at a dose of $2\times10^5$ cells. Lomitapide used in the two models was formulated with 45% saline, 40% PEG300, 5% Tween-80, and 10% DMSO.

Figure 18A:
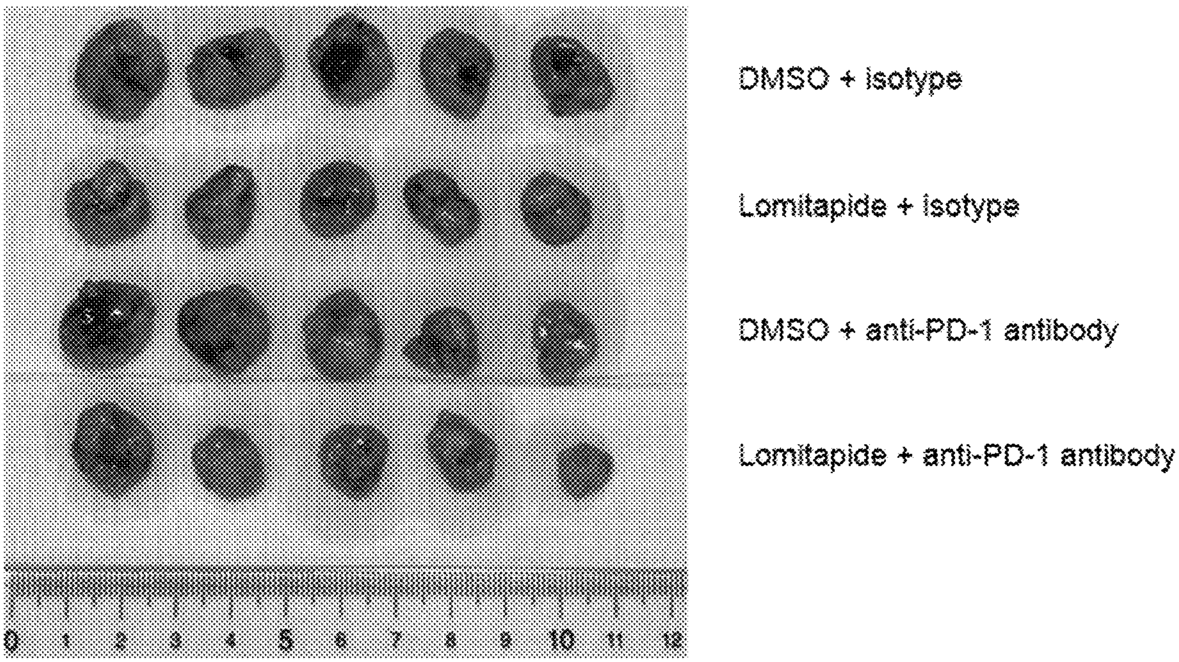
FIG. 18*a* is a photographic image showing synergistic efficacy of lomitapide and Anti-PD1 for the colorectal cancer cell line MC38 implanted into mice.
Figure 18B:
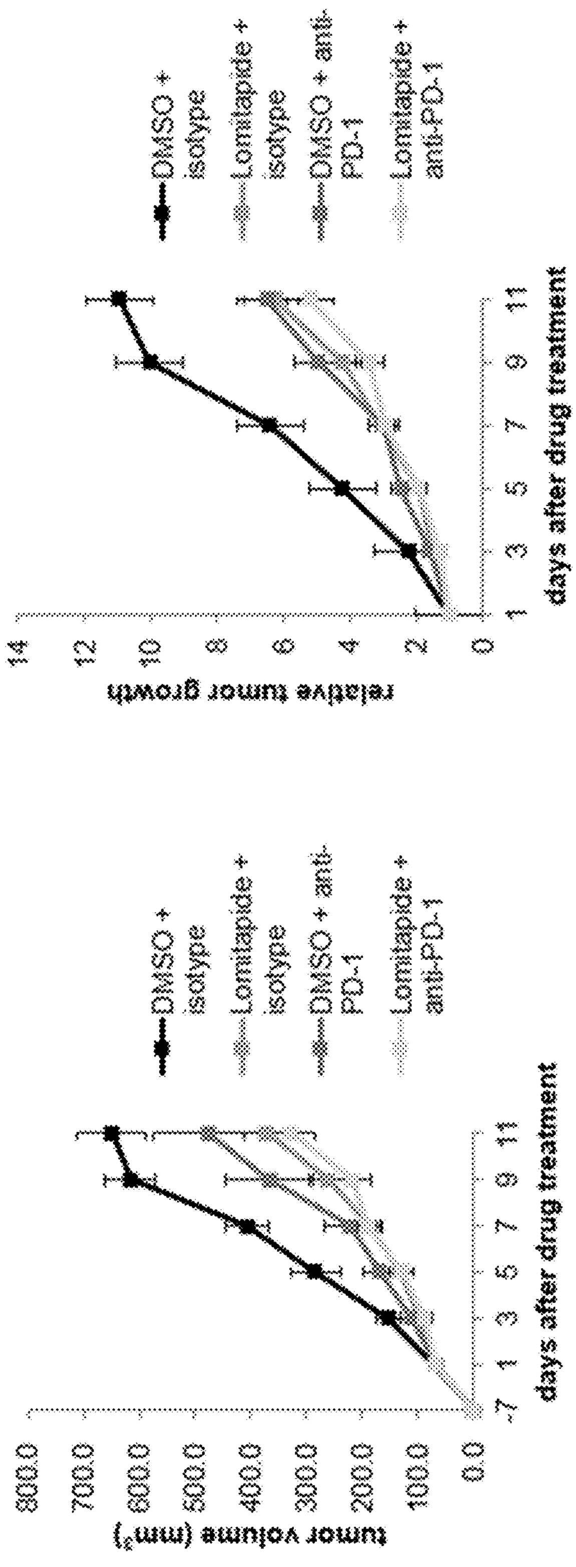
FIG. 18*b* shows the synergistic efficacy of lomitapide and anti-PD1 for the colorectal cancer cell line MC38 implanted into mice, as plotted for tumor volumes.

From 10 days after the DMC38 colorectal cancer cells injection, lomitapide was intraperitoneally injected five times at a dose of 20 mg/kg, and anti-PD-1 mAb (clone RMP1-14, BioXCell, West Lebanon, NH, USA) or rat IgG2a iso-type control (clone 2A3, BioXCell, BE0089) in PBS was administered at a dose of 10 mg/kg at days 1, 4, 7, and 10 (FIGS. 18*a* and 18*b*).

Figure 19A:
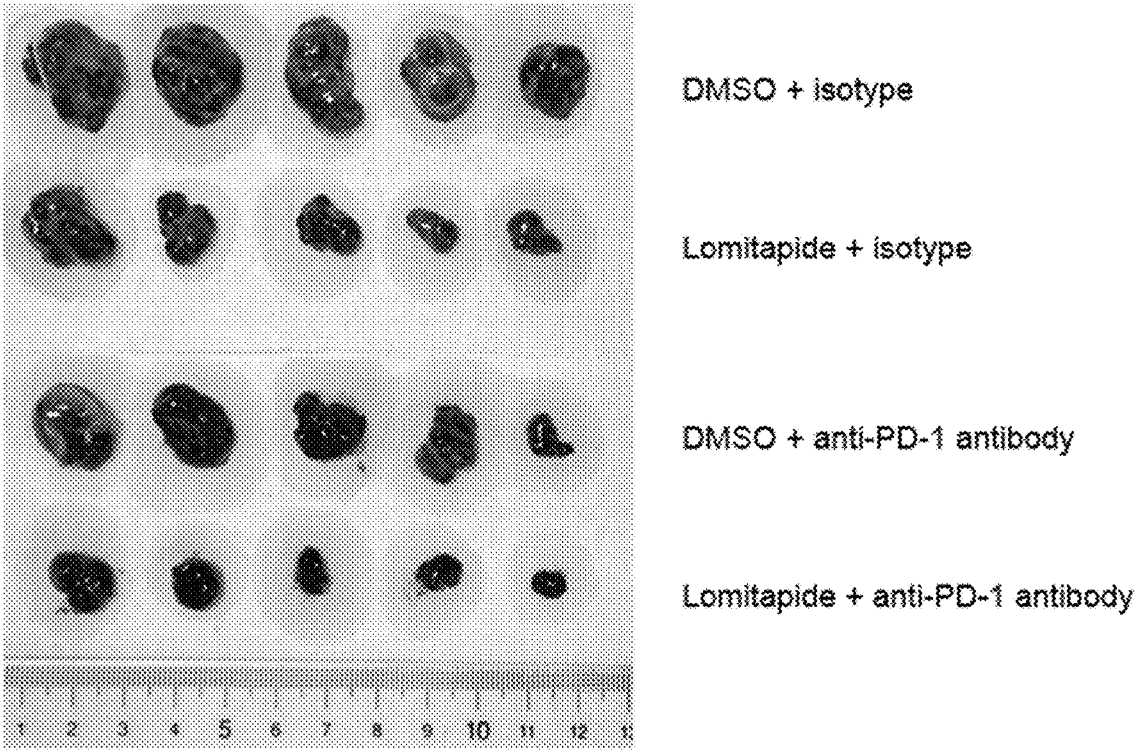
FIG. 19*a* is a photographic image showing synergistic efficacy of lomitapide and Anti-PD1 for the skin melanoma cell line B16F10 implanted into mice.
Figure 19B:
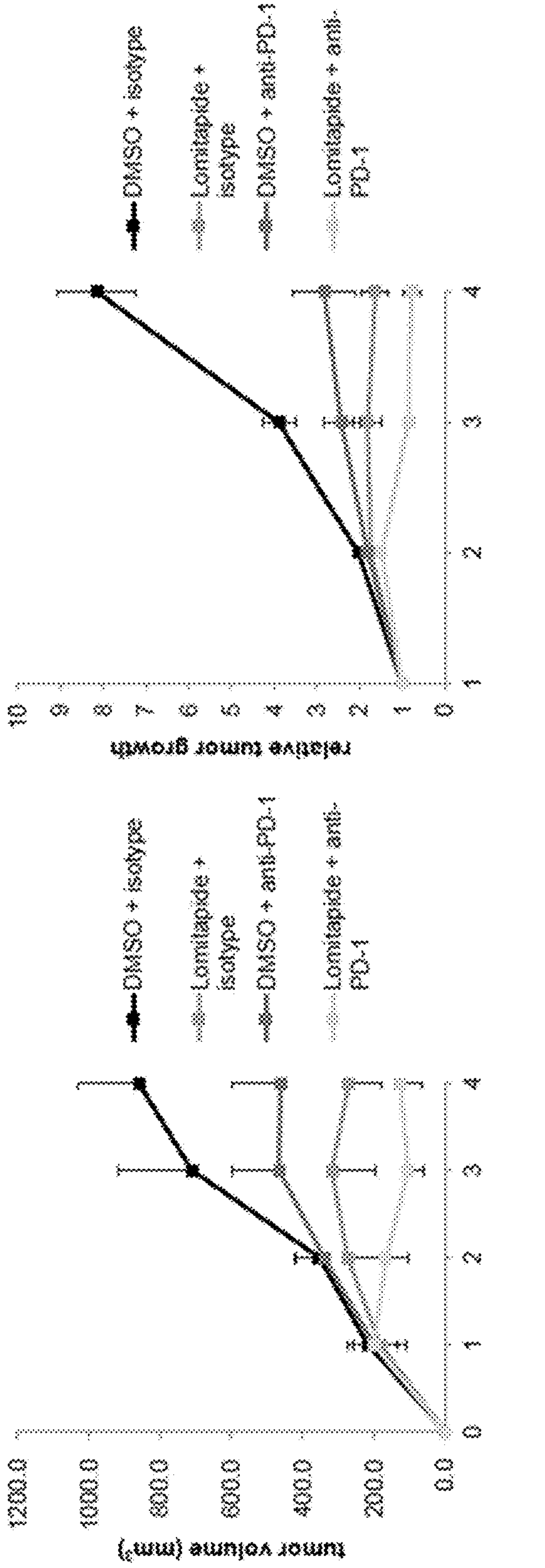
FIG. 19*b* shows the synergistic efficacy of lomitapide and anti-PD1 for the skin melanoma cell line B16F10 implanted into mice, as plotted for tumor volumes.

For B16F10 skin melanoma, from 10 days after the tumor injection, lomitapide was intraperitoneally injected at a dose of 40 mg/kg three times at days 3, 5, and 7, and anti-PD-1 mAb (clone RMP1-14, BioXCell, West Lebanon, NH, USA) or rat IgG2a iso-type control (clone 2A3, BioXCell, BE0089) was administered at a dose of 20 mg/kg at days 1, 3, 5, and 7. The mice were euthanized immediately when signs of pain were observed, the body weight was reduced by 20% compared to the normal weight, or the tumor volume exceeded 1,000 $mm^3$ (FIGS. 19*a* and 19*b*).

Through the two experiments, it was observed that lomitapide significantly suppressed and reduced tumor growth in the mouse homograft model, compared to the control. Even when compared to the test groups treated with the anti-PD-1 mAb, tumor growth was greatly suppressed and reduced in the lomitapide-treated group. Treatment with lomitapide and anti-PD-1 mAb in combination synergistically reduced the tumor size.

Figure 18C:
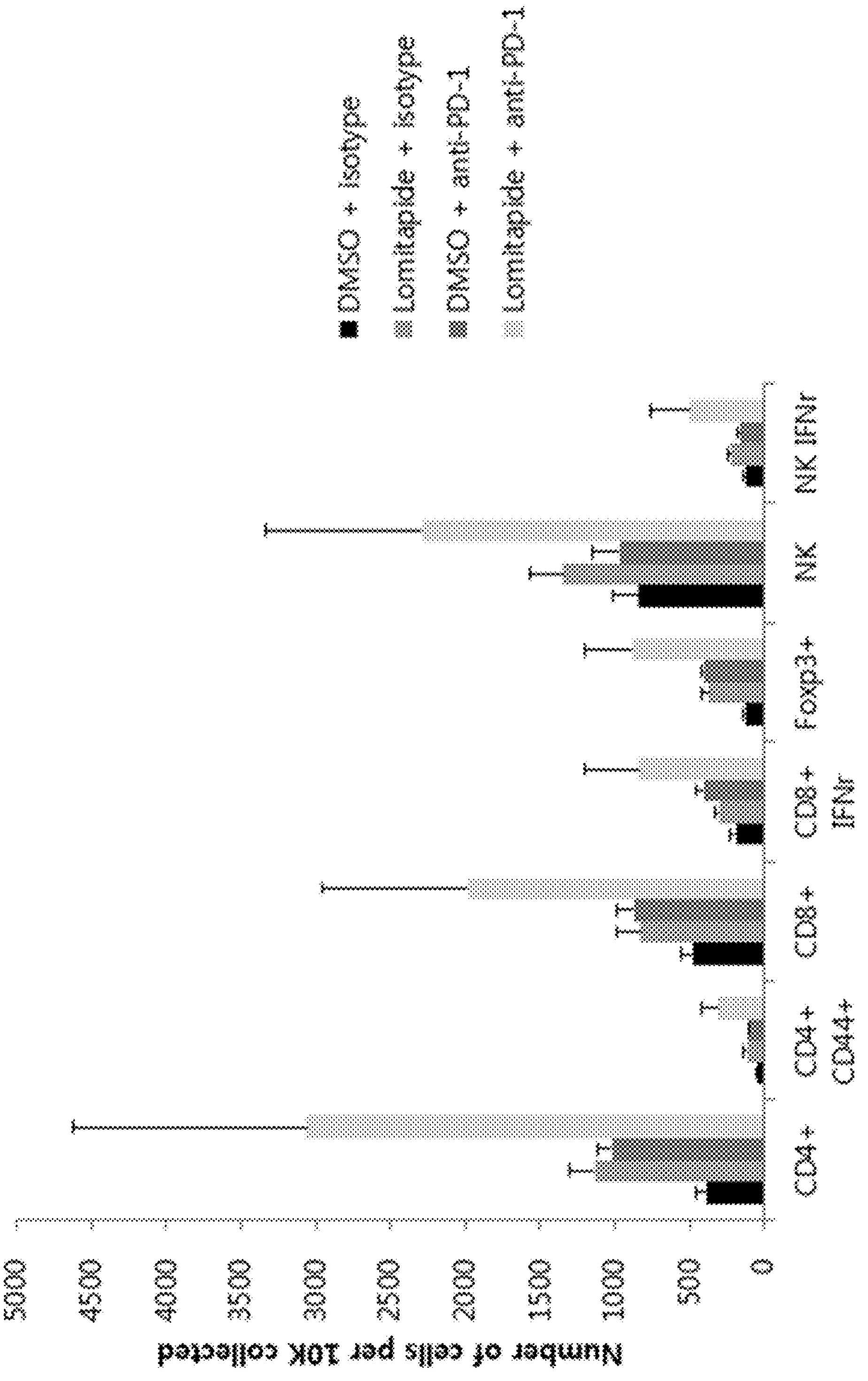
FIG. 18*c* shows the synergistic efficacy of lomitapide and anti-PD1 for the colorectal cancer cell line MC38 implanted into mice, as measured for immunocytes (CD4+, CD4+/CD44+, CD8+, CD8+/IFNη, Foxp3, NK, NK/IFNγ).

In addition, MC38 colorectal cancer cells were analyzed for immunocytes (CD4+, CD4+/CD44+, CD8+, CD8+/IFNη, Foxp3, NK, and NK/IFNγ). Levels of immunocytes in the group treated with lomitapide alone were observed to be superior (CD4+, NK, NK/IFNγ) or similar (CD4+/CD44+, CD8+, CD8+/IFNη, and Foxp3) to the group treated with anti-PD-1 mAb alone. All of the immunocytes were remarkably increased on the test group treated with the two drugs in combination (FIG. 18*c*).

Figure 20:
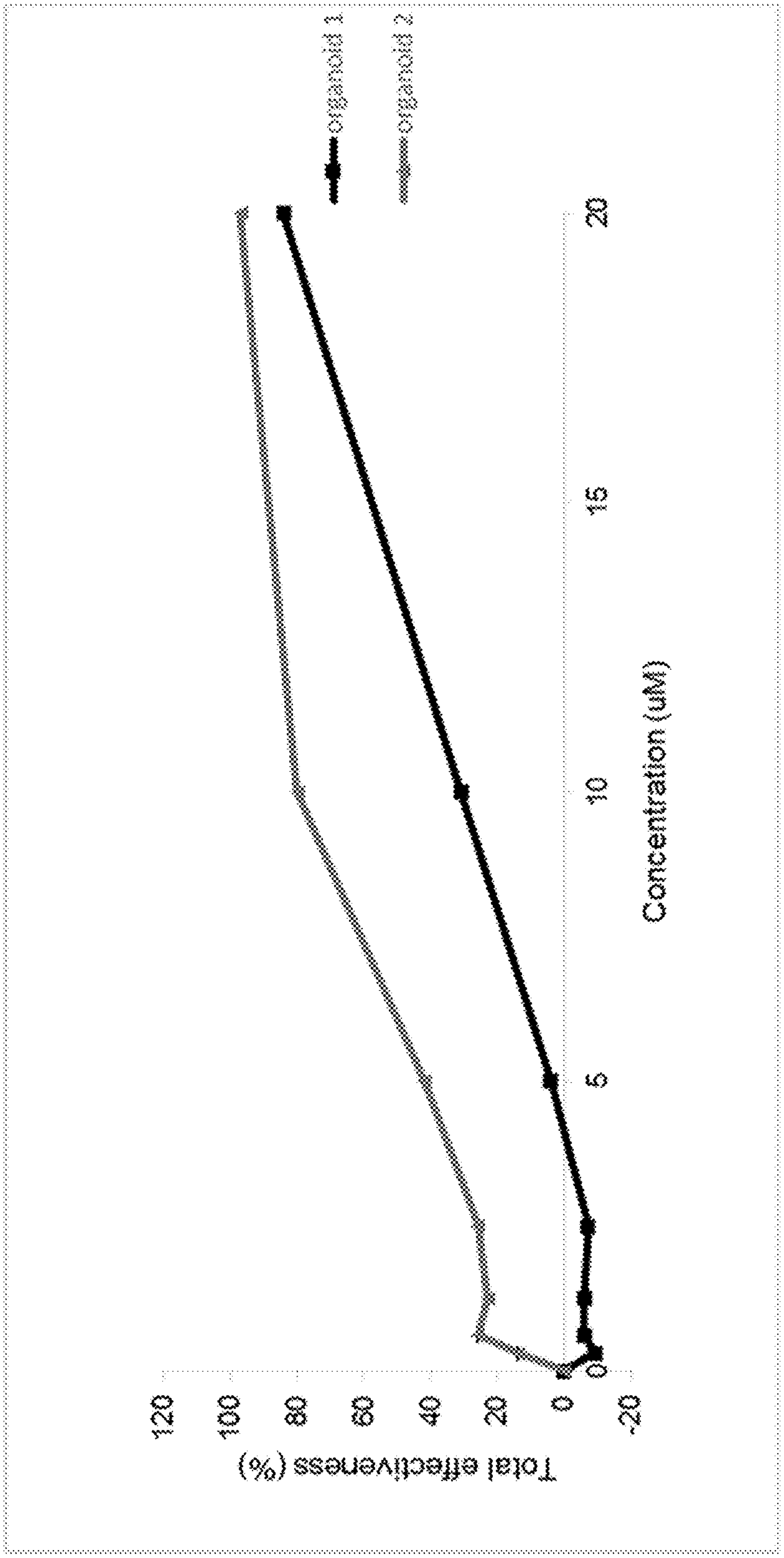
FIG. 20 is a plot of viability of the lomitapide-treated organoids derived from colorectal cancer patients.

Example 10: Viability Assay for Lomitapide-Treated Organoid Derived from Colorectal Cancer Patient Two-type colorectal cancer patient-derived organoids (organoid from males at 01-46 of age and organoid from females at 02-74 of age) were treated with lomitapide and assayed for viability as follows. The assay data showed that the organoids decreased in viability with the increase of the dose of lomitapide (FIG. 20), indicating that lomitapide is very effective for killing various colorectal cancer cells.

1. Imaging Based Evaluation of Drugs

Organoids derived from colorectal cancer patients were cultured for 5-7 days on 48-well plates (SPL, cat 32048).

The organoids were separated from the plates by pipetting with 200 μL of Dulbecco's phosphate-buffered saline (DPBS; Welgene LB001-02) and transferred to new tubes.

For staining, the separated organoids and Hoechst (Thermo, #H-1399) were added at a ratio of 1:2,000 to a culture medium and incubated for 30 minutes at 37° C. in a 5% $CO_2$ incubator.

After centrifugation of the stained organoids at 1,350 rpm for 3 minutes, the supernatant was removed.

The organoids were added in the same amount to each well of 96-well plates, followed by the same volume of a drug.

Following the dispense, the number, state, and area of organoids were measured through DAPI signals with the aid of the high-contents imaging-based screening device Cytation 5 (Biotek).

Subsequently, organoid areas were monitored three times every 24 hours for 72 hours without changing the culture medium.

The effectiveness of the drug was calculated by applying the raw data derived from Cytation 5 to the following formulas. In addition, the total effectiveness of the drug at a specific concentration is defined as a sum of organoid growth inhibition and organoid death.

Each organoid stained with Hoechst was measured for area ($\mu m^2$) by using Cytation 5, and areas of the all organoids in each well were summed.

The difference between the organoid area after 72 hours of drug treatment and the organoid area at the first 0 hour was calculated.

2. Evaluation Formula

In order to observe the organoid death induced by a drug at a specific concentration, a size change with the organoid death was calculated. In this regard, the size change was calculated as the ratio of the organoid area observed at 72 hours after drug treatment to the initial organoid area (formula 1).

The evaluation of overall efficacy can be calculated as the ratio of the damaged organoid of the drug-treated group to the damaged organoid ratio of the non-treated group after 72 hours of drug treatment (formula 2).

(Formula 1)

$$\text{Ratio of damaged organoid at specific concentration} = 1 - \frac{\text{organoid area after drug treatment (72 h)}}{\text{initial organoid area}}$$

(Formula 2)

$$\text{Effectiveness of Drug at specific concentration} = \frac{\text{Ratio of damaged organoid in drug-treated group}}{\text{Ratio of damaged organoid in non-treated group}} \times 100$$

Drug efficacy at specific concentration = Total effectiveness

In conclusion, the data obtained from the experiments in the Examples demonstrate that lomitapide inhibits the mTOR-mediated signal pathway and activates the cell autophagy mechanism, resulting in an anticancer effect. When used in combination with a conventional anticancer agent, lomitapide gives rise to a synergy effect.

What is claimed is:

1. A method for treating cancer comprising:

administering a composition comprising an mTOR signaling inhibitor as an active ingredient, wherein the mTOR signaling inhibitor is lomitapide, a pharmaceutically acceptable salt thereof, or an optical isomer thereof.

2. The method of claim 1, wherein the lomitapide is represented by the following Chemical Formula I:

[Chemical Formula I]

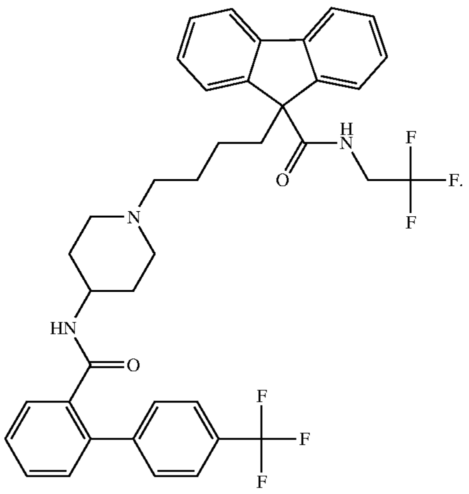

3. The method of claim 1, wherein the cancer is a solid cancer.

4. The method of claim 3, wherein the solid cancer is selected from the group consisting of melanoma, brain tumor, benign astrocytoma, malignant astrocytoma, pituitary adenoma, meningioma, central nervous system lymphoma, oligodendroglioma, ependymoma, brain stem tumor, head and neck tumor, laryngeal cancer, oropharyngeal cancer, nasal cavity cancer, nasopharyngeal cancer, salivary gland cancer, hypopharyngeal cancer, thyroid cancer, oral cavity carcinoma, thoracic tumor, small cell lung cancer, non-small cell lung cancer, thymus cancer, mediastinal tumor, esophageal cancer, breast cancer, male breast cancer, celioma, stomach cancer, liver cancer, cholangiocarcinoma, bile duct cancer, pancreatic cancer, small bowel cancer, large bowel cancer, rectal cancer, anal cancer, bladder cancer, kidney cancer, male genital tumor, penis cancer, prostate cancer, female genital cancer, cervical cancer, endometrial cancer, ovarian cancer, uterine sarcoma, vaginal cancer, vulva cancer, female urethral cancer, bone tumor, duodenal cancer, fibrosarcoma, and skin cancer.

5. The method of claim 1, wherein the cancer is a blood cancer.

6. The method of claim 5, wherein the blood cancer is selected from the group consisting of acute myeloid leukemia, acute lymphocytic leukemia, chronic myeloid leukemia, chronic lymphocytic leukemia, acute monocytic leukemia, multiple myeloma, Hodgkin's lymphoma, and non-Hodgkin's lymphoma.

7. The method of claim 1, wherein the composition further comprises an anticancer agent.

8. The method of claim 7, wherein the anticancer agent is selected from the group consisting of fluorouracil, irinotecan, an anti-PD1 antibody, bevacizumab, capecitabine, cetuximab, ramucirumab, oxaliplatin, ipilimumab, pembrolizumab, leucovorin, trifluridine/tipiracil, nivolumab, panitumumab, regorafenib, aflibercept, and a combination thereof.

9. The method of claim 8, wherein the anticancer agent is selected from the group consisting of fluorouracil, irinotecan, an anti-PD1 antibody, and a combination thereof.

* * * * *